US008652496B2

(12) United States Patent
Barak

(10) Patent No.: US 8,652,496 B2
(45) Date of Patent: Feb. 18, 2014

(54) BIOCIDES AND APPARATUS

(75) Inventor: Ayala Barak, Tel Aviv (IL)

(73) Assignee: A.Y. Laboratories Ltd., Tel Aviv (IL)

(*) Notice: Subject to any disclaimer, the term of this patent is extended or adjusted under 35 U.S.C. 154(b) by 434 days.

(21) Appl. No.: 12/731,917

(22) Filed: Mar. 25, 2010

(65) Prior Publication Data

US 2010/0183746 A1 Jul. 22, 2010

Related U.S. Application Data

(63) Continuation of application No. 11/056,405, filed on Feb. 14, 2005, now Pat. No. 7,837,883, which is a continuation-in-part of application No. PCT/IL2005/000007, filed on Jan. 3, 2005.

(60) Provisional application No. 60/536,851, filed on Jan. 14, 2004, provisional application No. 60/536,811, filed on Jan. 14, 2004, provisional application No. 60/536,852, filed on Jan. 14, 2004, provisional application No. 60/536,853, filed on Jan. 14, 2004.

(51) Int. Cl.
| | |
|---|---|
| *A01N 25/00* | (2006.01) |
| *A01N 37/12* | (2006.01) |
| *A01N 37/44* | (2006.01) |
| *A01N 47/10* | (2006.01) |
| *A61K 31/27* | (2006.01) |

(52) U.S. Cl.
USPC ........... 424/405; 210/756; 210/764; 514/476; 514/561

(58) Field of Classification Search
None
See application file for complete search history.

(56) References Cited

U.S. PATENT DOCUMENTS

| | | | |
|---|---|---|---|
| 3,344,018 | A | 9/1967 | Shibe et al. |
| 3,920,832 | A | 11/1975 | Barer et al. |
| 4,476,930 | A | 10/1984 | Watanabe |
| 5,565,109 | A | 10/1996 | Sweeny |
| 5,795,487 | A | 8/1998 | Dallmier et al. |
| 5,976,386 | A | 11/1999 | Barak |
| 6,110,387 | A | 8/2000 | Choudhury et al. |
| 6,132,628 | A | 10/2000 | Barak |
| 6,429,181 | B2 | 8/2002 | Sweeny et al. |
| 6,471,974 | B1 | 10/2002 | Rees et al. |
| 6,478,972 | B1 | 11/2002 | Shim et al. |
| 6,533,958 | B2 | 3/2003 | Shim et al. |
| 2003/0121868 | A1 | 7/2003 | Barak |
| 2006/0054563 | A1 | 3/2006 | Tsuneki et al. |

FOREIGN PATENT DOCUMENTS

| | | |
|---|---|---|
| EP | 0517102 | 9/1992 |
| GB | 1600289 | 10/1981 |
| WO | WO0100029 A1 | 1/2001 |
| WO | 03/096810 A1 | 11/2003 |
| WO | 2005019117 A1 | 3/2005 |

OTHER PUBLICATIONS

G. Degramont, "Water Treatment Handbook", Springer-Verlag 1991, pp. 249-250 (1991).

(Continued)

*Primary Examiner* — Daniel Sullivan
*Assistant Examiner* — Barbara Frazier
(74) *Attorney, Agent, or Firm* — Browdy and Neimark, PLLC

(57) ABSTRACT

A biocide is formed by mixing at least one of ammonium sulfamate and ammonium carbamate with an aqueous solution of a hypochlorite oxidant at a molar ratio of ammonium to hypochlorite of at least 1:1. The biocide is useful in treating microbial or biofilm growth, pulp and paper process water, cooling tower water, waste water, reclaimed waste water, sludge, colloidal suspensions, irrigation water or a medium having a reducing capacity.

17 Claims, 2 Drawing Sheets

(56) References Cited

OTHER PUBLICATIONS

Burrows et al, "The equilibrium between ammonium carbonate and ammonium carbamate in aqueous solution at 25°," Publication of the Research Laboratory of Physical Chemistry, Massachusetts Institute of Technology, Boston, Mass., No. 84, pp. 993-995 (Jun. 12, 1912).

Fenton, "On the limited hydration of ammonium carbamate," Chem. Sco. Jour. 33, 300, pp. 386-393 (Dec. 10, 1885).

Wen et al , "Ammonium Carbonate, Ammonium Bicarbonate, and Ammonium Carbamate Equilibria: a Raman Study," J. Phys. Chem, vol. 99, No. 1, pp. 359-368 (1995).

An Office Action dated Jul. 29, 2010, which issued during the prosecution of Applicant's Israel Patent Application No. 176814. (translation of relevant section attached).

An Office Action dated Apr. 17, 2013, which issued during the prosecution of U.S. Appl. No. 10/586,349.

A Supplementary European Search Report dated Jan. 25, 2012 which issued during the prosecution of Applicant's EP 05703082 (four pages).

Search Report dated Jan. 5, 2012 which issued during the prosecution of Applicant's ROC (Taiwan) App. No. 094101192 (one page).

Wilson et al, Toxicologic Effects of Ammonium Carbamate and Related Compounds, Am. J. Vet. Res., vol. 29, No. 4, pp. 897-906 (Apr. 1968).

BIOCIDES AND APPARATUS

CROSS-REFERENCE TO RELATED APPLICATIONS

This application is a continuation of U.S. patent application Ser. No. 11/056,405, filed Feb. 14, 2005, which is a continuation-in-part of PCT/IL2005/00007, filed Jan. 12, 2005 and claims the benefit of priority from U.S. Provisional Patent Application Ser. Nos. 60/536,851, 60/536,811, 60/536,853 and 60/536,852, all of which were filed on Jan. 14, 2004. The contents of all of these applications are incorporated herein by reference.

FIELD OF THE INVENTION

The invention relates to method and apparatus for inhibiting the growth of living organisms.

BACKGROUND

U.S. Pat. Nos. 5,795,487, 5,976,386, 6,110,387, 6,132,628, 6,429,181, 6,478,972, and 6,533,958, British Patent No. GB 1600289, and published U.S. Patent Application No. 20030121868, the contents of all of which are incorporated herein by reference, are believed to represent relevant prior art.

SUMMARY OF THE INVENTION

In some embodiments of the invention, there are provided methods for controlling microbial or biofilm growth in a medium. Common to these embodiments of the invention, the medium is selected from the group consisting of pulp and paper factory process water, cooling tower water, waste water, reclaimed waste water, clay slurries, starch slurries, sludge, soil, colloidal suspension, and irrigation water, and strongly reducing solutions, and the method comprises mixing a nitrogen-containing compound having at least one primary, secondary or tertiary nitrogen atom, or a salt thereof, with a solution of hypochlorite oxidant to form a biocide, the molar ratio of primary, secondary and tertiary nitrogen atoms in the at least one compound to hypochlorite being at least 1:1, and applying the biocide to the medium.

It will be appreciated that although the term "biocide" is used throughout the present description and claims, in some embodiments of the invention killing of microorganisms need not be effected in order to achieve control of microbial growth or biofilm growth.

It will also be appreciated that in some parts of the description and claims, reference is made to a hypochlorite solution or to a solution of hypochlorite, whereas in other parts of the description and claims, reference is made to a hypochlorite dilution which is prepared from a hypochlorite solution. Irrespective of the term used, in those embodiments of the invention in which hypochlorite is mixed with a nitrogen-containing compound, the concentration of the hypochlorite should not be higher than 24,000 ppm as total chlorine immediately prior to mixing with the nitrogen-containing compound.

It will be appreciated that the mixing of the compound containing at least one primary, secondary or tertiary nitrogen atom, or salt thereof, with hypochlorite will take place in solution, and that in solution the compound containing at least one primary, secondary or tertiary nitrogen atom, or the salt thereof, may be in equilibrium with an ionized, tautomeric or other form which is different than the form the compound has when not in solution. It will also be appreciated that when salts of such compounds are used, in solution there may be equilibria involving proton exchange between the components of the salt themselves and/or between one or more components of the salt and solvent. Thus, throughout the specification and claims, when reference is made to a compound containing at least one primary, secondary or tertiary nitrogen atom, or a salt thereof, or to sub-groups of such a compound or a salt thereof, e.g. a compound of the formula $R^1R^2N$-A-B or salt thereof, it will be understood that this expression is meant to encompass all protonated, de-protonated, and tautomeric forms of the compound or salt thereof which may exist in solution at the time of mixing with hypochlorite.

In some embodiments of the invention, a nitrogen-containing compound which is an amphoteric molecule containing at least one moiety selected from the group consisting of COOH and $SO_3H$ and at least one moiety selected from the group consisting of a primary amine moiety, a secondary amine moiety, and a tertiary amine moiety is employed. In other embodiments of the invention, an anionic form of such an amphoteric molecule is employed, and in some of those embodiments, the counterion is of the form $[NH_2R^3R^4]^+$ wherein $R^3$ and $R^4$ are defined below.

It will be appreciated that when reference is made to a salt of the form $Y^{x-}[NH_2R^3R^4]^+$ or $Y^{x-}[NHR^3R^4Cl]^+$, and it is stated that Y is an acid, the acidity of this acid is considered in relation to the compound $NHR^3R^4$.

There is provided, in accordance with an embodiment of the invention, a method for controlling microbial or biofilm growth in a medium, the method comprising mixing a salt of the formula $Y^{x-}[NH_2R^3R^4]^+_x$ and an aqueous solution of a hypochlorite oxidant to form a biocide, wherein $Y^{x-}$ is a basic form of an acid Y that contains at least one moiety selected from the group consisting of a primary amine moiety, a secondary amine moiety, a tertiary amine moiety, an amide moiety, an imide moiety, a sulfamide moiety, a sulfamide moiety, and an amineimine moiety; and $[NH_2R^3R^4]^+$ is an acidic form of a base $NHR^3R^4$ wherein:

$R^3$ and $R^4$ are each independently selected from the group consisting of H and $C_{1-8}$ alkyl, or $R^3$ and $R^4$, together with the nitrogen atom to which they are attached, form a 5- to 10-member heterocyclic ring optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl; and x is 1 to 3;

and the molar ratio of $[NH_2R^3R^4]^+$ to hypochlorite is at least 1:1, and applying the biocide to the medium.

In accordance with some variations of this embodiment of the invention, Y is selected from the group consisting of straight, branched and cyclic molecules containing at least one moiety selected from the group consisting of an amide moiety, an imide moiety, a sulfamide moiety, a sulfimide moiety, and an amineimine moiety, and $Y^{x-}$ is a basic form of the molecule. In some variations of this embodiment of the invention, in $Y^{x-}$ at least one of the at least one amide moiety, imide moiety, sulfamide moiety, sulfimide moiety, or amineimine moiety is ionized to the corresponding anionic form.

In accordance with some variations of this embodiment of the invention, Y is selected from the group consisting of amphoteric molecules containing at least one moiety selected from the group consisting of COOH and $SO_3H$ and at least one moiety selected from the group consisting of a primary amine moiety, a secondary amine moiety, and a tertiary amine moiety, and $Y^{x-}$ is an anionic form of the amphoteric molecule. In some variations of this embodiment of the invention, at least one of the at least one COOH and $SO_3H$ is ionized to the corresponding anionic form.

In accordance with some variations of this embodiment of the invention, $Y^{x-}$ is of the formula $[R^1R^2N\text{-}A\text{-}COO]^{x-}$ or $[R^1R^2N\text{-}A\text{-}SO_3]^{x-}$, wherein:

A is a bond, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_{4}\text{-}C_{20}$ alkylcycloalkyl, $C_{4-10}$ cycloalkenyl, $C_{4-10}$ cycloalkynyl, or $C_6\text{-}C_{10}$ aryl, wherein each $C_{1-20}$ alkyl, $C_{2-20}$ alkenyl, $C_{2-20}$ alkynyl, $C_{3-10}$ cycloalkyl, $C_4\text{-}C_{20}$ alkylcycloalkyl, $C_{4-10}$ cycloalkenyl, $C_{4-10}$ cycloalkynyl or $C_6\text{-}C_{10}$ aryl is optionally substituted with one or more groups selected from —COOH, —COH, —$SCH_3$, —$NH_2$, =NH, —NHC(=NH)$NH_2$, —C(=O)$NH_2$, —OH, 4-hydroxyphenyl, 5-imidazolyl, 3-indolyl, halogen, —$SO_3H$, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —$SO_2R^7$ or —$NHR^7$ wherein $R^7$ is H, $C_{1-8}$ alkyl, phenyl, 4-methylphenyl, benzyl or and wherein each $C_{1-20}$ alkyl, $C_{2-20}$ alkenyl, $C_{2-20}$ alkynyl, $C_{3-10}$ cycloalkyl, $C_4\text{-}C_{20}$ alkylcycloalkyl, $C_{4-10}$ cycloalkenyl, $C_{4-10}$ cycloalkynyl or $C_6\text{-}C_{10}$ aryl optionally contains one to three heteroatoms selected from N, O and S;

$R^1$ and $R^2$ are each independently selected from the group consisting of H, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4\text{-}C_{20}$ alkylcycloalkyl, $C_{4-10}$ cycloalkenyl, $C_{4-10}$ cycloalkynyl, or $C_6\text{-}C_{10}$ aryl, wherein each $C_{1-20}$ alkyl, $C_{2-20}$ alkenyl, $C_{2-20}$ alkynyl, $C_{3-10}$ cycloalkyl, $C_4\text{-}C_{20}$ alkylcycloalkyl, $C_{4-10}$ cycloalkenyl, $C_{4-10}$ cycloalkynyl or $C_6\text{-}C_{10}$ aryl is optionally substituted with one or more groups selected from —COOH, —COH, —$SCH_3$, —$NH_2$, =NH, —NHC(=NH)$NH_2$, —C(=O)$NH_2$, —OH, 4-hydroxyphenyl, 5-imidazolyl, 3-indolyl, halogen, —$SO_3H$, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —$SO_2R^7$ or —$NHR^7$ wherein $R^7$ is H, $C_{1-8}$ alkyl, phenyl, 4-methylphenyl, benzyl or —$NH_2$, and wherein each $C_{1-20}$ alkyl, $C_{2-20}$ alkenyl, $C_{2-20}$ alkynyl, $C_{3-10}$ cycloalkyl, $C_4\text{-}C_{20}$ alkylcycloalkyl, $C_{4-10}$ cycloalkenyl, $C_{4-10}$ cycloalkynyl or $C_6\text{-}C_{10}$ aryl optionally contains one to three heteroatoms selected from N, O and S;

or $R^1$ and A, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl;

or $R^1$ and $R^2$, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl.

In accordance with some variations of this embodiment of the invention, the concentration of the hypochlorite oxidant in the aqueous hypochlorite oxidant solution immediately prior to mixing with the salt or mixtures of salts is not more than 24,000 ppm as total chlorine. In accordance with some variations of this embodiment of the invention, the concentration of the hypochlorite oxidant in the aqueous hypochlorite oxidant solution immediately prior to mixing with the salt or mixtures of salts is not more than 12,000 ppm as total chlorine.

In accordance with some variations of this embodiment of the invention, the salt or mixture of salts is in an aqueous solution at a concentration of 0.5-60% w/v immediately prior to mixing with the hypochlorite oxidant solution.

In accordance with some variations of this embodiment of the invention, the mixing takes place in a mixing chamber into and out of which there is a continuous flow of water during the mixing.

In accordance with some variations of this embodiment of the invention, the biocide is applied to the medium substantially as the biocide is formed. In accordance with other variations of this embodiment of the invention, the biocide is applied to the medium within 30 seconds of formation of the biocide. In accordance with other variations of this embodiment of the invention, the biocide is applied to the medium within 60 seconds of formation of the biocide. In accordance with other variations of this embodiment of the invention, the biocide is applied to the medium within 90 seconds of formation of the biocide. In accordance with other variations of this embodiment of the invention, the biocide is applied to the medium within 120 seconds of formation of the biocide. In accordance with other variations of this embodiment of the invention, the biocide is applied to the medium within 150 seconds of formation of the biocide. In accordance with other variations of this embodiment of the invention, the biocide is applied to the medium within 180 seconds of formation of the biocide.

In accordance with some variations of this embodiment of the invention, the mixing chamber is a conduit.

In accordance with other variations of this embodiment of the invention, the mixing takes place in a mixing chamber out of which there is not a continuous flow of water during the mixing. In accordance with other variations of this embodiment of the invention, biocide is applied to the medium substantially immediately upon completion of the mixing. In accordance with other variations of this embodiment of the invention, the biocide is applied to the medium within 30 seconds of completion of the mixing. In accordance with other variations of this embodiment of the invention, the biocide is applied to the medium within 60 seconds of completion of the mixing. In accordance with other variations of this embodiment of the invention, the biocide is applied to the medium within 90 seconds of completion of the mixing. In accordance with other variations of this embodiment of the invention, the biocide is applied to the medium within 120 seconds of completion of the mixing. In accordance with other variations of this embodiment of the invention, the biocide is applied to the medium within 150 seconds of completion of the mixing. In accordance with other variations of this embodiment of the invention, the biocide is applied to the medium within 180 seconds of completion of the mixing.

In accordance with some variations of this embodiment of the invention, the hypochlorite oxidant is selected from the group consisting of alkaline and alkali earth metal hypochlorites, hypochlorites released to water from a stable chlorine carrier and hypochlorite formed in situ from chlorine gas, and mixtures thereof. In accordance with some variations of this embodiment of the invention, the stable chlorine carrier is selected from the group consisting of trichlorocyanuric acid, dichlorodimethylhydantoin and monochlorodimethylhydantoin. In accordance with some variations of this embodiment of the invention, the hypochlorite oxidant is selected from the group consisting of lithium hypochlorite, sodium hypochlorite, calcium hypochlorite, magnesium hypochlorite and potassium hypochlorite. In accordance with some variations of this embodiment of the invention, the hypochlorite oxidant is sodium hypochlorite.

In accordance with some variations of this embodiment of the invention, $R^3$ and $R^4$ are both H. In accordance with other variations of this embodiment of the invention, one of $R^3$ and $R^4$ is H and the other is not. In accordance with other variations of this embodiment of the invention, neither $R^3$ nor $R^4$ is H.

In accordance with some variations of this embodiment of the invention, Y is selected from the group consisting of carbamic acid, sulfamic acid, glycine, glutamine, arginine, histidine, and lysine, and mixture thereof. In accordance with some variations of this embodiment of the invention, Y is selected from the group consisting of melamine, cyanuric acid, hydantoin, dialkyl hydantoin such as dimethyl hydantoin, biuret, succinamide, succinimide, creatine, and creatinine, and mixtures thereof.

In accordance with some variations of this embodiment of the invention, the molar ratio of $[NH_2R^3R^4]^+$ to the hypochlorite oxidant is 1:1. In accordance with other variations of this embodiment of the invention, the molar ratio of $[NH_2R^3R^4]^+$ to the hypochlorite oxidant is greater than 1:1.

In accordance with some variations of this embodiment of the invention, the concentration of the hypochlorite oxidant in the aqueous hypochlorite oxidant solution immediately prior to mixing with the salt or mixture of salts is not more than 24,000 ppm expressed as total chlorine, and the mixing chamber comprises a conduit through which water flows as the hypochlorite oxidant solution and the salt or mixture of salts are mixed. In accordance with some variations of this embodiment of the invention, the concentration of the hypochlorite oxidant in the aqueous hypochlorite oxidant solution immediately prior to mixing with the salt or mixture of salts is not more than 12,000 ppm as total chlorine. In accordance with some variations of this embodiment of the invention, the solution of hypochlorite oxidant is prepared in situ in the conduit prior to addition of the solution of the salt or mixture of salts to the conduit.

In accordance with some variations of this embodiment of the invention, the salt or mixture of salts is diluted prior to mixing with the hypochlorite oxidant.

In accordance with some variations of this embodiment of the invention, the biocide has a pH of between 8.0 and 11.5 immediately prior to being applied to the medium. In accordance with some variations of this embodiment of the invention, the biocide has a pH of at least 8.5 immediately prior to being applied to the medium. In accordance with some variations of this embodiment of the invention, the biocide has a pH of at least 9.0 immediately prior to being applied to the medium. In accordance with some variations of this embodiment of the invention, the biocide has a pH of at least 9.5 immediately prior to being applied to the medium. In accordance with some variations of this embodiment of the invention, the biocide has a pH of at least 10.0 immediately prior to being applied to the medium. In accordance with some variations of this embodiment of the invention, the biocide has a pH of at least 10.5 immediately prior to being applied to the medium. In accordance with some variations of this embodiment of the invention, the biocide has a pH of at least 11.0 immediately prior to being applied to the medium. In accordance with some variations of this embodiment of the invention, the biocide has a pH of no more than 11.5 immediately prior to being applied to the medium.

In accordance with some variations of this embodiment of the invention, the medium is selected from the group consisting of pulp and paper factory water, cooling tower water, waste water, reclaimed waste water, clay slurries, starch slurries, sludge, soil, colloidal suspensions, and irrigation water. In accordance with some variations of this embodiment of the invention, the medium is pulp and paper factory process water. In accordance with some variations of this embodiment of the invention, the medium is cooling tower water. In accordance with some variations of this embodiment of the invention, the medium is waste water. In accordance with some variations of this embodiment of the invention, the medium is reclaimed waste water. In accordance with some variations of this embodiment of the invention, the medium is a clay slurry. In accordance with some variations of this embodiment of the invention, the medium is a starch slurry. In accordance with some variations of this embodiment of the invention, the medium is a sludge. In accordance with some variations of this embodiment of the invention, the medium is a colloidal suspension. In accordance with some variations of this embodiment of the invention, the medium is irrigation water. In accordance with some variations of this embodiment of the invention, the medium is a medium containing strong reducing agents or having a high reducing capacity, viz. an ORP of not greater than 150 millivolts.

In accordance with some variations of this embodiment of the invention, the hypochlorite oxidant and the salt or mixture of salts are mixed in the absence of added bromide and the medium is substantially free of added bromide during application of the biocide. In accordance with some variations of this embodiment of the invention, bromide is not added to the medium as a component to supplement or enhance the biocide.

In accordance with some variations of this embodiment of the invention, the biocide is applied to the medium periodically with a duty cycle of less than 1:2. In accordance with some variations of this embodiment of the invention, the biocide is applied to the medium periodically with a duty cycle of between about 1:5 and 1:10. In accordance with some variations of this embodiment of the invention, the biocide is applied to the medium periodically with a duty cycle of less than 1:10. In accordance with some variations of this embodiment of the invention, the biocide is applied to the medium periodically with a duty cycle of less than 1:25. In accordance with some variations of this embodiment of the invention, the biocide is applied to the medium periodically with a duty cycle of less than 1:50.

In accordance with some variations of this embodiment of the invention, the biocide is applied to the medium at a rate to maintain in the biocide a stable pH of at least 8.0 as the biocide is produced.

In accordance with some variations of this embodiment of the invention, the concentration of the biocide immediately prior to being applied to the medium is from 1000 to 12,000 ppm expressed as total chlorine.

In accordance with some variations of this embodiment of the invention, the medium has a pH of between about 5 and about 11.5 before the biocide is applied to the medium. In accordance with some variations of this embodiment of the invention, the medium has a pH of between about 6 and about 10 before the biocide is applied to the medium. In accordance with some variations of this embodiment of the invention, the medium has a pH of between about 7 and about 9 before the biocide is applied to the medium.

In accordance with some variations of this embodiment of the invention, the concentration of the biocide in the medium, upon application of the biocide to the medium, is 0.5-300 ppm expressed as total chlorine. In accordance with some variations of this embodiment of the invention, the concentration of the biocide in the medium, upon application of the biocide to the medium, is 1-10 ppm expressed as chlorine.

In accordance with some variations of this embodiment of the invention, the biocide is effective within 24 hours of application to the medium. In accordance with some variations of this embodiment of the invention, the biocide is effective within 1 hour of application to the medium. In accordance with some variations of this embodiment of the invention, the biocide is effective within 20 minutes of application to the medium. In accordance with some variations of this embodiment of the invention, the biocide is effective within 15 minutes of application to the medium.

In accordance with some variations of this embodiment of the invention, the biocide is capable of reducing microbial activity by at least 50% within 3 hours after administration. In accordance with some variations of this embodiment of the invention, the biocide is capable of reducing microbial activity by at least 50% within 1 hour after administration. In accordance with some variations of this embodiment of the invention, the biocide is capable of reducing microbial activity by at least 50% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of reducing microbial activity by at least 75% within 3 hours after administration. In accordance with some variations of this embodiment of the invention, the biocide is capable of reducing microbial activity by at least 75% within 1 hour after administration. In accordance with some variations of this embodiment of the invention, the biocide is capable of reducing microbial activity by at least 75% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of reducing microbial activity by at least 90% within 3 hours after administration. In accordance with some variations of this embodiment of the invention, the biocide is capable of reducing microbial activity by at least 90% within 1 hour after administration. In accordance with some variations of this embodiment of the invention, the biocide is capable of reducing microbial activity by at least 90% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of killing at least 50% of the microorganisms in a liquid test sample within 3 hours after administration. In accordance with some variations of this embodiment of the invention, the biocide is capable of killing at least 50% of the microorganisms in a liquid test sample within 1 hour after administration. In accordance with some variations of this embodiment of the invention, the biocide is capable of killing at least 50% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the biocide is capable of killing at least 75% of the microorganisms in a liquid test sample within 3 hours after administration. In accordance with some variations of this embodiment of the invention, the biocide is capable of killing at least 75% of the microorganisms in a liquid test sample within 1 hour after administration. In accordance with some variations of this embodiment of the invention, the biocide is capable of killing at least 75% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the biocide is capable of killing at least 90% of the microorganisms in a liquid test sample within 3 hours after administration. In accordance with some variations of this embodiment of the invention, the biocide is capable of killing at least 90% of the microorganisms in a liquid test sample within 1 hour after administration. In accordance with some variations of this embodiment of the invention, the biocide is capable of killing at least 90% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

There is also provided, in accordance with an embodiment of the invention, apparatus for applying a biocide to a medium, comprising:

a salt-containing reservoir containing a salt of the formula $Y^{x-}[NH_2R^3R^4]^+_x$, or a mixture of such salts, wherein $Y^{x-}$ is a basic form of an acid Y that contains at least one moiety selected from the group consisting of a primary amine moiety, a secondary amine moiety, a tertiary amine moiety, an amide moiety, an imide moiety, a sulfamide moiety, a sulfimide moiety, and an amineimine moiety;

$[NH_2R^3R^4]^+$ is an acidic form of a base $NHR^3R^4$ wherein:

$R^3$ and $R^4$ are each independently selected from the group consisting of H and $C_{1-8}$ alkyl, or $R^3$ and $R^4$, together with the nitrogen atom to which they are attached, form a 5- to 10-member heterocyclic ring optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl; and and x is 1 to 3;

a source of hypochlorite oxidant dilution having a concentration of not more than 24,000 ppm expressed as total chlorine, and a mixing chamber operable to mix the dilution and the salt or mixture of salts in a molar ratio of $[NH_2R^3R^4]^+$ to hypochlorite of at least 1:1, to produce the biocide in the mixing chamber.

In some variations of this embodiment of the invention, the source of hypochlorite oxidant dilution has a concentration of not more than 12,000 ppm as total chlorine.

In some variations of this embodiment of the invention, Y is selected from the group consisting of straight, branched and cyclic molecules containing at least one moiety selected from the group consisting of an amide moiety, an imide moiety, a sulfamide moiety, a sulfimide moiety, and an amineimine moiety, and $Y^{x-}$ is basic form of the molecule. In some variations of this embodiment of the invention, at least one of the at least one amide moiety, imide moiety, sulfamide moiety, sulfimide moiety, or amineimine moiety is ionized to the corresponding anionic form.

In some variations of this embodiment of the invention, Y is an amphoteric molecule containing at least one moiety selected from the group consisting of COOH and $SO_3H$ and at least one moiety selected from the group consisting of a primary amine moiety, a secondary amine moiety, and a tertiary amine moiety, and $Y^{x-}$ is an anionic form of the amphoteric molecule. In some variations of this embodiment of the invention, at least one of the at least one COOH and $SO_3H$ is ionized to the corresponding anionic form.

In accordance with some variations of this embodiment of the invention, the salt or mixture of salts is present in the salt-containing reservoir as an aqueous solution.

In accordance with some variations of this embodiment of the invention, the source of hypochlorite oxidant dilution comprises a hypochlorite-containing reservoir containing a hypochlorite oxidant solution, and a diluter operable to dilute the hypochlorite oxidant solution to produce the hypochlorite oxidant dilution having a concentration of not more than 24,000 ppm expressed as total chlorine. In accordance with some variations of this embodiment of the invention, the diluter is operable to dilute the hypochlorite oxidant solution to produce the hypochlorite oxidant dilution having a concentration of not more than 12,000 ppm as total chlorine. In accordance with some variations of this embodiment of the invention, the diluter and the mixing chamber are a single conduit which is adapted to dilute the hypochlorite oxidant prior to mixing with the salt or mixture of salts.

In accordance with some variations of this embodiment of the invention, the apparatus further comprising an egress adapted to enable application of the biocide from the mixing chamber to the medium.

There is also provided, in accordance with an embodiment of the invention, a salt of the formula $Y^{x-}[NHR^3R^4Cl]^+_x$, wherein $Y^{x-}$ is a basic form of an acid Y that contains at least one moiety selected from the group consisting of a primary amine moiety, a secondary amine moiety, a tertiary amine moiety, an amide moiety, an imide moiety, a sulfamide moiety, a sulfimide moiety, and an amineimine moiety; and $[NHR^3R^4Cl]^+$ is an acidic form of a base $NHR^3R^4$ wherein:

$R^3$ and $R^4$ are each independently selected from the group consisting of H and $C_{1-8}$ alkyl, or $R^3$ and $R^4$, together with the nitrogen atom to which they are attached, form a 5- to 10-member heterocyclic ring optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl; and x is 1 to 3.

In accordance with some variations of this embodiment of the invention, Y is selected from the group consisting of straight, branched and cyclic molecules containing at least one moiety selected from the group consisting of an amide moiety, an imide moiety, a sulfamide moiety, a sulfimide moiety, and an amineimine moiety, and $Y^{x-}$ is basic form of the molecule. In accordance with some variations of this embodiment of the invention, at least one of the at least one amide moiety, imide moiety, sulfamide moiety, sulfimide moiety, or amineimine moiety is ionized to the corresponding anionic form.

In accordance with some variations of this embodiment of the invention, Y is selected from the group consisting of amphoteric molecules containing at least one moiety selected from the group consisting of a primary amine moiety, a secondary amine moiety, and a tertiary amine moiety, and at least one moiety selected from the group consisting of COOH and $SO_3H$, and $Y^{x-}$ is an anionic form of the amphoteric molecule. In accordance with some variations of this embodiment of the invention, at least one of the at least one COOH and $SO_3H$ is ionized to the corresponding anionic form.

In accordance with some variations of this embodiment of the invention, $Y^{x-}$ is of the formula $[R^1R^2N\text{-}A\text{-}COO]^{x-}$ or $[R^1R^2N\text{-}A\text{-}SO_3]^{x-}$, wherein:

A is a bond, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —SCH$_3$, —NH$_2$, =NH, —NHC(=NH)NH$_2$, —C(=O)NH$_2$, —OH, 4-hydroxyphenyl, 5-imidazolyl, 3-indolyl, halogen, —SO$_3$H, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —SO$_2$R$^7$ or —NHR$^7$ wherein R$^7$ is H, $C_{1-8}$ alkyl, phenyl, 4-methylphenyl, benzyl or —NH$_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

R$^1$ and R$^2$ are each independently selected from the group consisting of H, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —SCH$_3$, —NH$_2$, =NH, —NHC(=NH)NH$_2$, —C(=O)NH$_2$, —OH, 4-hydroxyphenyl, 5-imidazolyl, 3-indolyl, halogen, —SO$_3$H, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —SO$_2$R$^7$ or —NHR$^7$ wherein R$^7$ is H, $C_{1-8}$ alkyl, phenyl, 4-methylphenyl, benzyl or —NH$_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

or R$^1$ and A, together with the nitrogen atom to which they are attached, form a 5- to 10-member heterocyclic ring or a 5- to 10-member heteroaromatic ring in which the free electron pair of the nitrogen atom to which R$^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —OC$_{1-6}$ alkyl or —OC$_{3-8}$ cycloalkyl;

or R$^1$ and R$^2$, together with the nitrogen atom to which they are attached, form a 5- to 10-member heterocyclic ring or a 5- to 10-member heteroaromatic ring in which the free electron pair of the nitrogen atom to which R$^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —OC$_{1-6}$ alkyl or —OC$_{3-8}$ cycloalkyl.

In accordance with some variations of this embodiment of the invention, Y is selected from the group consisting of carbamic acid, sulfamic acid, glycine, glutamine, arginine, histidine, and lysine.

In accordance with some variations of this embodiment of the invention, Y is selected from the group consisting of melamine, cyanuric acid, hydantoin, dialkyl hydantoin, biuret, succinamide, succinimide, creatine, and creatinine.

There is also provided, in accordance with an embodiment of the invention, a molecular species selected from the group consisting of compounds of the formulae [R$^1$R$^2$NCl-A-COO] and [R$^1$R$^2$NCl-A-SO$_3$] and ions of the formulae [R$^1$NCl-A-COO]$^-$ and [R$^1$NCl-A-SO3]$^-$, and tautomers thereof, wherein A, R$^1$ and R$^2$ are as defined above.

In accordance with some variations of this embodiment of the invention, the molecular species is an N-chlorocarbamate, an N-chlorosulfamate, an N-chloro ammonium carbamate, or an N-chloro ammonium sulfamate.

There is also provided, in accordance with another embodiment of the invention, a method for controlling microbial or biofilm growth in a medium, the method comprising mixing a nitrogen-containing compound or mixture of such compounds selected from the group consisting of:

salts of the formula $Y^{x-}Z^{n+}_{x/n}$, wherein x and $Y^{x-}$ are as defined above, and Z$^+$ is a cation other than a cation of the form [NH$_2$R$^3$R$^4$]$^+$ as defined above wherein n is a whole number greater than zero; and amphoteric molecules Q containing at least one moiety selected from the group consisting of COOH and SO$_3$H and at least one moiety selected from the group consisting of a primary amine moiety, a secondary amine moiety, and a tertiary amine moiety;

and an aqueous solution of a hypochlorite oxidant to form a biocide, wherein the molar ratio of nitrogen atoms in the nitrogen-containing compound to the hypochlorite is at least 1:1, and applying the biocide to the medium.

In accordance with some variations of this embodiment of the invention, Y is selected from the group consisting of straight, branched and cyclic molecules containing at least one moiety selected from the group consisting of an amide moiety, an imide moiety, a sulfamide moiety, a sulfimide moiety, and an amineimine moiety, and $Y^{x-}$ is a basic form of the molecule. In some variations of this embodiment of the invention, in $Y^{x-}$ at least one of the at least one amide moiety, imide moiety, sulfamide moiety, sulfimide moiety, or amineimine moiety is ionized to the corresponding anionic form.

In accordance with some variations of this embodiment of the invention, Y is selected from the group consisting of amphoteric molecules containing at least one moiety selected from the group consisting of COOH and SO$_3$H and at least one moiety selected from the group consisting of a primary amine moiety, a secondary amine moiety, and a tertiary amine moiety, and $Y^{x-}$ is an anionic form of the amphoteric molecule. In some variations of this embodiment of the invention, at least one of the at least one COOH and SO$_3$H is ionized to the corresponding anionic form.

In accordance with some variations of this embodiment of the invention, $Y^{x-}$ is of the formula [R$^1$R$^2$N-A-COO]$^{x-}$ or [R$^1$R$^2$N-A-SO$_3$]$^{x-}$, wherein:

A is a bond, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —SCH$_3$, —NH$_2$, =NH, —NHC(=NH)NH$_2$, —C(=O)NH$_2$, —OH, 4-hydroxyphenyl, 5-imidazolyl, 3-indolyl, halogen, —SO$_3$H, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —SO$_2$R$^7$ or —NHR$^7$ wherein R$^7$ is H, $C_{1-8}$ alkyl, phenyl, 4-methylphenyl, benzyl or —NH$_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

$R^1$ and $R^2$ are each independently selected from the group consisting of H, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —SCH$_3$, —NH$_2$, =NH, —NHC(=NH)NH$_2$, —C(=O)NH$_2$, —OH, 4-hydroxyphenyl, 5-imidazolyl, 3-indolyl, halogen, —SO$_3$H, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —SO$_2$R$^7$ or —NHR$^7$ wherein R$^7$ is H, $C_{1-8}$ alkyl, phenyl, 4-methylphenyl, benzyl or —NH$_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

or $R^1$ and A, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —OC$_{1-6}$ alkyl or —OC$_{3-8}$ cycloalkyl;

or $R^1$ and $R^2$, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —OC$_{1-6}$ alkyl or —OC$_{3-8}$ cycloalkyl.

In accordance with some variations of this embodiment of the invention, Q is of the formula $R^1R^2$N-A-COOH or $R^1R^2$N-A-SO$_3$H, wherein:

A is a bond, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —SCH$_3$, —NH$_2$, =NH, —NHC(=NH)NH$_2$, —C(=O)NH$_2$, —OH, 4-hydroxyphenyl, 5-imidazolyl, 3-indolyl, halogen, —SO$_3$H, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{1-8}$ cycloalkyl, —O—$C_{4-9}$ cycloalkylalkyl, —O-phenyl, —O-4-methylphenyl, —O-benzyl, —SO$_2$R$^7$ or —NHR$^7$ wherein R$^7$ is H, $C_{1-8}$ alkyl, phenyl, 4-methylphenyl, benzyl or —NH$_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

$R^1$ and $R^2$ are each independently selected from the group consisting of H, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —SCH$_3$, —NH$_2$, =NH, —NHC(=NH)NH$_2$, —C(=O)NH$_2$, —OH, 4-hydroxyphenyl, 5-imidazolyl, 3-indolyl, halogen, —SO$_3$H, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —SO$_2$R$^7$ or —NHR$^7$ wherein R$^7$ is H, $C_{1-8}$ alkyl, phenyl, 4-methylphenyl, benzyl or —NH$_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

or $R^1$ and A, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{1-8}$ cycloalkyl, halogen, hydroxy, —OC$_{1-6}$ alkyl or —OC$_{3-8}$ cycloalkyl;

or $R^1$ and $R^2$, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —OC$_{1-6}$ alkyl or —OC$_{3-8}$ cycloalkyl;

or a salt thereof.

In accordance with some variations of this embodiment of the invention, the nitrogen-containing compound is salt of creatinine, cyanuric acid, melamine, or dialkylhydantoin.

In accordance with some variations of this embodiment of the invention, the concentration of the hypochlorite oxidant in the aqueous hypochlorite oxidant solution immediately prior to mixing with the nitrogen-containing compound is not more than 24,000 ppm as total chlorine. In accordance with some variations of this embodiment of the invention, the concentration of the hypochlorite oxidant in the aqueous hypochlorite oxidant solution immediately prior to mixing with the nitrogen-containing compound is not more than 12,000 ppm as total chlorine.

In accordance with some variations of this embodiment of the invention, the nitrogen-containing compound or mixture thereof is in an aqueous solution at a concentration of 0.5-60% w/v prior to mixing with the hypochlorite oxidant solution.

In accordance with some variations of this embodiment of the invention, the mixing takes place in a mixing chamber into and out of which there is a continuous flow of water during the mixing.

In accordance with some variations of this embodiment of the invention, the biocide is applied to the medium substantially as the biocide is formed. In accordance with other variations of this embodiment of the invention, the biocide is applied to the medium within 30 seconds of formation of the biocide. In accordance with other variations of this embodiment of the invention, the biocide is applied to the medium within 60 seconds of formation of the biocide. In accordance with other variations of this embodiment of the invention, the biocide is applied to the medium within 90 seconds of formation of the biocide. In accordance with other variations of this embodiment of the invention, the biocide is applied to the medium within 120 seconds of formation of the biocide. In accordance with other variations of this embodiment of the invention, the biocide is applied to the medium within 150 seconds of formation of the biocide. In accordance with other variations of this embodiment of the invention, the biocide is applied to the medium within 180 seconds of formation of the biocide.

In accordance with some variations of this embodiment of the invention, the mixing chamber is a conduit.

In accordance with other variations of this embodiment of the invention, the mixing takes place in a mixing chamber out of which there is not a continuous flow of water during the mixing. In accordance with other variations of this embodiment of the invention, biocide is applied to the medium substantially immediately upon completion of the mixing. In accordance with other variations of this embodiment of the invention, the biocide is applied to the medium within 30 seconds of completion of the mixing. In accordance with other variations of this embodiment of the invention, the biocide is applied to the medium within 60 seconds of completion of the mixing. In accordance with other variations of this embodiment of the invention, the biocide is applied to the medium within 90 seconds of completion of the mixing. In accordance with other variations of this embodiment of the invention, the biocide is applied to the medium within 120 seconds of completion of the mixing. In accordance with other variations of this embodiment of the invention, the biocide is applied to the medium within 150 seconds of completion of the mixing. In accordance with other variations of this embodiment of the invention, the biocide is applied to the medium within 180 seconds of completion of the mixing.

In accordance with some variations of this embodiment of the invention, the hypochlorite oxidant is selected from the group consisting of alkaline and alkali earth metal hypochlorites, hypochlorite released to water from a stable chlorine carrier and hypochlorite formed in situ from chlorine gas, and mixtures thereof. In accordance with some variations of this embodiment of the invention, the stable chlorine carrier is selected from the group consisting of trichlorocyanuric acid, dichlorodimethylhydantoin and monochlorodimethylhydantoin. In accordance with some variations of this embodiment of the invention, the hypochlorite oxidant is selected from the group consisting of lithium hypochlorite, sodium hypochlorite, calcium hypochlorite, magnesium hypochlorite and potassium hypochlorite. In accordance with some variations of this embodiment of the invention, the hypochlorite oxidant is sodium hypochlorite.

In accordance with some variations of this embodiment of the invention, the nitrogen-containing compound is selected from the group consisting of carbamic acid, sulfamic acid, glycine, glutamine, arginine, histidine, lysine, and mixtures thereof.

In accordance with some variations of this embodiment of the invention, Y is selected from the group consisting of carbamic acid, sulfamic acid, glycine, glutamine, arginine, histidine, and lysine.

In accordance with some variations of this embodiment of the invention, the molar ratio of nitrogen atoms in the nitrogen-containing compound or mixture thereof to the hypochlorite oxidant is 1:1. In accordance with some variations of this embodiment of the invention, the molar ratio of the nitrogen-containing compound to the hypochlorite oxidant is 1:1. In accordance with some variations of this embodiment of the invention, the molar ratio of nitrogen atoms in the nitrogen-containing compound or mixture thereof to the hypochlorite oxidant is greater than 1:1. In accordance with other variations of this embodiment of the invention, the molar ratio of the nitrogen-containing compound to the hypochlorite oxidant is greater than 1:1.

In accordance with some variations of this embodiment of the invention, the concentration of the hypochlorite oxidant in the aqueous hypochlorite oxidant solution prior to mixing with the nitrogen-containing compound is not more than 24,000 ppm as total chlorine, and the mixing chamber comprises a conduit through which water flows as the hypochlorite oxidant solution and the nitrogen-containing compound are mixed. In accordance with some variations of this embodiment of the invention, the concentration of the hypochlorite oxidant in the aqueous hypochlorite oxidant solution immediately prior to mixing with the nitrogen-containing compound is not more than 12,000 ppm as total chlorine. In accordance with some variations of this embodiment of the invention, the solution of hypochlorite oxidant is prepared in situ in the conduit prior to addition of the solution of the nitrogen-containing compound to the conduit.

In accordance with some variations of this embodiment of the invention, the nitrogen-containing compound is diluted prior to mixing with the hypochlorite oxidant.

In accordance with some variations of this embodiment of the invention, the biocide has a pH of between 8.0 and 11.5 immediately prior to being applied to the medium. In accordance with some variations of this embodiment of the invention, the biocide has a pH of at least 8.5 immediately prior to being applied to the medium. In accordance with some variations of this embodiment of the invention, the biocide has a pH of at least 9.0 immediately prior to being applied to the medium. In accordance with some variations of this embodiment of the invention, the biocide has a pH of at least 9.5 immediately prior to being applied to the medium. In accordance with some variations of this embodiment of the invention, the biocide has a pH of at least 10.0 immediately prior to being applied to the medium. In accordance with some variations of this embodiment of the invention, the biocide has a pH of at least 10.5 immediately prior to being applied to the medium. In accordance with some variations of this embodiment of the invention, the biocide has a pH of at least 11.0 immediately prior to being applied to the medium. In accordance with some variations of this embodiment of the invention, the biocide has a pH of no more than 11.5 immediately prior to being applied to the medium.

In accordance with some variations of this embodiment of the invention, the medium is selected from the group consisting of pulp and paper factory water, cooling tower water, waste water, reclaimed waste water, clay slurries, starch slurries, sludge, soil, colloidal suspension, and irrigation water. In accordance with some variations of this embodiment of the invention, the medium is pulp and paper factory process water. In accordance with some variations of this embodiment of the invention, the medium is cooling tower water. In accordance with some variations of this embodiment of the invention, the medium is waste water. In accordance with some variations of this embodiment of the invention, the medium is reclaimed waste water. In accordance with some variations of this embodiment of the invention, the medium is a clay slurry. In accordance with some variations of this embodiment of the invention, the medium is a starch slurry. In accordance with some variations of this embodiment of the invention, the medium is a sludge. In accordance with some variations of this embodiment of the invention, the medium is soil. In accordance with some variations of this embodiment of the invention, the medium is a colloidal suspension. In accordance with some variations of this embodiment of the invention, the medium is irrigation water. In accordance with some variations of this embodiment of the invention, the medium is a medium containing strong reducing agents or having a high reducing capacity, viz. an ORP of not greater than 150 millivolts.

In accordance with some variations of this embodiment of the invention, the hypochlorite oxidant and the nitrogen-containing compound are mixed in the absence of added bromide and the medium is substantially free of added bromide during application of the biocide. In accordance with some variations of this embodiment of the invention, bromide is not added to the medium as a component to supplement or enhance the biocide.

In accordance with some variations of this embodiment of the invention, the biocide is applied to the medium periodically with a duty cycle of less than 1:2. In accordance with some variations of this embodiment of the invention, the biocide is applied to the medium periodically with a duty cycle of between about 1:5 and 1:10. In accordance with some variations of this embodiment of the invention, the biocide is applied to the medium periodically with a duty cycle of less than 1:10. In accordance with some variations of this embodiment of the invention, the biocide is applied to the medium periodically with a duty cycle of less than 1:25. In accordance with some variations of this embodiment of the invention, the biocide is applied to the medium periodically with a duty cycle of less than 1:50.

In accordance with some variations of this embodiment of the invention, the biocide is applied to the medium at a rate to maintain in the biocide a stable pH of at least 8.0 as the biocide is produced.

In accordance with some variations of this embodiment of the invention, the concentration of the biocide immediately prior to being applied to the medium is from 1000 to 12,000 ppm expressed as total chlorine.

In accordance with some variations of this embodiment of the invention, the medium has a pH of between about 5 and about 11.5 before the biocide is applied to the medium. In accordance with sonic variations of this embodiment of the invention, the medium has a pH of between about 6 and about 10 before the biocide is applied to the medium. In accordance with some variations of this embodiment of the invention, the medium has a pH of between about 7 and about 9 before the biocide is applied to the medium.

In accordance with some variations of this embodiment of the invention, the concentration of the biocide in the medium, upon application of the biocide to the medium, is 0.5-300 ppm expressed as chlorine. In accordance with some variations of this embodiment of the invention, the concentration of the biocide in the medium, upon application of the biocide to the medium, is 1-10 ppm expressed as chlorine.

In accordance with some variations of this embodiment of the invention, the biocide is effective within 24 hours of application to the medium. In accordance with some variations of this embodiment of the invention, the biocide is effective within 1 hour of application to the medium. In accordance with some variations of this embodiment of the invention, the biocide is effective within 20 minutes of application to the medium. In accordance with some variations of this embodiment of the invention, the biocide is effective within 15 minutes of application to the medium.

In accordance with some variations of this embodiment of the invention, the biocide is capable of reducing microbial activity by at least 50% within 3 hours after administration. In accordance with some variations of this embodiment of the invention, the biocide is capable of reducing microbial activity by at least 50% within 1 hour after administration. In accordance with some variations of this embodiment of the invention, the biocide is capable of reducing microbial activity by at least 50% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of reducing microbial activity by at least 75% within 3 hours after administration. In accordance with some variations of this embodiment of the invention, the biocide is capable of reducing microbial activity by at least 75% within 1 hour after administration. In accordance with some variations of this embodiment of the invention, the biocide is capable of reducing microbial activity by at least 75% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of reducing microbial activity by at least 90% within 3 hours after administration. In accordance with some variations of this embodiment of the invention, the biocide is capable of reducing microbial activity by at least 90% within 1 hour after administration. In accordance with some variations of this embodiment of the invention, the biocide is capable of reducing microbial activity by at least 90% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of killing at least 50% of the microorganisms in a liquid test sample within 3 hours after administration. In accordance with some variations of this embodiment of the invention, the biocide is capable of killing at least 50% of the microorganisms in a liquid test sample within 1 hour after administration. In accordance with some variations of this embodiment of the invention, the biocide is capable of killing at least 50% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the biocide is capable of killing at least 75% of the microorganisms in a liquid test sample within 3 hours after administration. In accordance with some variations of this embodiment of the invention, the biocide is capable of killing at least 75% of the microorganisms in a liquid test sample within 1 hour after administration. In accordance with some variations of this embodiment of the invention, the biocide is capable of killing at least 75% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the biocide is capable of killing at least 90% of the microorganisms in a liquid test sample within 3 hours after administration. In accordance with some variations of this embodiment of the invention, the biocide is capable of killing at least 90% of the microorganisms in a liquid test sample within 1 hour after administration. In accordance with some variations of this embodiment of the invention, the biocide is capable of killing at least 90% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the medium is present in a system from which a portion of the medium is discharged and replaced during the regular course of operation of the system. In accordance with some variations of this embodiment of the invention, the portion of the medium which is discharged and replaced during the regular course of operation of the system is continuously discharged and replaced during the regular course of operation of the system. In accordance with some variations of this embodiment of the invention, the portion of the medium which is discharged and replaced during the regular course of operation of the system is discharged and replaced at least once every 24 hours during the regular course of operation of the system.

There is also provided, in accordance with an embodiment of the invention, an apparatus for applying a biocide to a medium, comprising:

a nitrogen-containing compound reservoir containing a nitrogen-containing compound or mixture thereof selected from the group consisting of:

salts of the formula $Y^{x-}Z^{n+}_{x/n}$, wherein x and $Y^{x-}$ are as defined above, $Z^+$ is a cation other than a cation of the form $[NH_2R^3R^4]^+$ as defined above, and n is a whole number greater than zero; and amphoteric molecules Q containing at least one moiety selected from the group consisting of COOH and $SO_3H$ and at least one moiety selected from the group consisting of a primary amine moiety, a secondary amine moiety, and a tertiary amine moiety;

a source of hypochlorite oxidant dilution having a concentration of between not more than 24,000 ppm as total chlorine, and a mixing chamber operable to mix the dilution and the nitrogen-containing compound or mixture thereof in a molar ratio of nitrogen atoms in the nitrogen-containing compound to the hypochlorite of at least 1:1, to produce the biocide in the mixing chamber.

In some variations of this embodiment of the invention, the source of hypochlorite oxidant dilution has a concentration of not more than 12,000 ppm as total chlorine.

In some variations of this embodiment of the invention, Y is selected from the group consisting of straight, branched and cyclic molecules containing at least one moiety selected from the group consisting of an amide moiety, an imide moiety, a sulfamide moiety, a sulfimide moiety, and an amineimine moiety, and $Y^{x-}$ is basic form of the molecule. In some variations of this embodiment of the invention, at least one of the at least one amide moiety, imide moiety, sulfamide moiety, sulfimide moiety, or amineimine moiety is ionized to the corresponding anionic form.

In some variations of this embodiment of the invention, Y is an amphoteric molecule containing at least one moiety selected from the group consisting of COOH and $SO_3H$ and at least one moiety selected from the group consisting of a primary amine moiety, a secondary amine moiety, and a tertiary amine moiety, and $Y^{x-}$ is an anionic form of the amphoteric molecule. In some variations of this embodiment of the invention, at least one of the at least one COOH and $SO_3H$ is ionized to the corresponding anionic form.

In some variations of this embodiment of the invention, Q is an amphoteric molecule containing at least one moiety selected from the group consisting of COOH and $SO_3H$ and at least one moiety selected from the group consisting of a primary amine moiety, a secondary amine moiety, and a tertiary amine moiety, and $Y^{x-}$ is an anionic form of the amphoteric molecule.

In accordance with some variations of this embodiment of the invention, the source of hypochlorite oxidant dilution comprises a hypochlorite-containing reservoir containing a hypochlorite oxidant solution, and a diluter operable to dilute the hypochlorite oxidant solution to produce the hypochlorite oxidant dilution having a concentration of not more than 24,000 ppm expressed as total chlorine. In accordance with some variations of this embodiment of the invention, the diluter is operable to dilute the hypochlorite oxidant solution to produce the hypochlorite oxidant dilution having a concentration of not more than 12,000 ppm as total chlorine. In accordance with some variations of this embodiment of the invention, the diluter and the mixing chamber are a single conduit which is adapted to dilute the hypochlorite oxidant prior to mixing with the salt or mixture of salts.

In accordance with some variations of this embodiment of the invention, the nitrogen-containing compound is present in nitrogen-compound containing reservoir as an aqueous solution.

In accordance with some variations of this embodiment of the invention, the molar ratio of nitrogen atoms in the nitrogen-containing compound or mixture thereof to the hypochlorite oxidant is 1:1. In accordance with some variations of this embodiment of the invention, the molar ratio of the nitrogen-containing compound to the hypochlorite oxidant is 1:1. In accordance with some variations of this embodiment of the invention, the molar ratio of nitrogen atoms in the nitrogen-containing compound or mixture thereof to the hypochlorite oxidant is greater than 1:1. In accordance with other variations of this embodiment of the invention, the molar ratio of the nitrogen-containing compound to the hypochlorite oxidant is greater than 1:1.

In accordance with some variations of this embodiment of the invention, the apparatus further comprising an egress adapted to enable application of the biocide from the mixing chamber to the medium.

There is also provided, in accordance with an embodiment of the invention, a method for controlling microbial or biofilm growth in a medium, the method comprising mixing a nitrogen-containing compound, a bromide and an aqueous solution of a hypochlorite oxidant to form a biocide, the nitrogen-containing compound being selected from the group consisting of salts of the formula $Y^{x-}[NH_2R^3R^4]^+_x$, salts of the formula $Y^{x-}Z^{n+}_{x/n}$, and molecules Y per se, wherein Z and n are as defined above, $Y^{x-}$ is a basic form of an acid Y that contains at least one moiety selected from the group consisting of a primary amine moiety, a secondary amine moiety, a tertiary amine moiety, an amide moiety, an imide moiety, a sulfamide moiety, a sulfimide moiety, and an amineimine moiety; and $[NH_2R^3R^4]^+$ is an acidic form of a base $NHR^3R^4$ wherein:

$R^3$ and $R^4$ are each independently selected from the group consisting of H and $C_{1-8}$ alkyl, or $R^3$ and $R^4$, together with the nitrogen atom to which they are attached, form a 5- to 10-member heterocyclic ring optionally substituted by one or more groups selected from $C_{1-6}$ alkyl, $C_{3-8}$ cycloalkyl, halogen, hydroxy, $-OC_{1-6}$ alkyl or $-OC_{3-8}$ cycloalkyl; and x is 1 to 3;

and the molar ratio of nitrogen atoms in the nitrogen-containing compound to hypochlorite is at least 1:1, and applying the biocide to the medium.

In accordance with some variations of this embodiment of the invention, Y is selected from the group consisting of straight, branched and cyclic molecules containing at least one moiety selected from the group consisting of an amide moiety, an imide moiety, a sulfamide moiety, a sulfimide moiety, and an amineimine moiety, and $Y^{x-}$ is a basic form of the molecule. In some variations of this embodiment of the invention, in $Y^{x-}$ at least one of the at least one amide moiety, imide moiety, sulfamide moiety, sulfimide moiety, or amineimine moiety is ionized to the corresponding anionic form.

In accordance with some variations of this embodiment of the invention, Y is selected from the group consisting of amphoteric molecules containing at least one moiety selected from the group consisting of COOH and $SO_3H$ and at least one moiety selected from the group consisting of a primary amine moiety, a secondary amine moiety, and a tertiary amine moiety, and $Y^{x-}$ is an anionic form of the amphoteric molecule. In some variations of this embodiment of the invention, at least one of the at least one COOH and $SO_3H$ is ionized to the corresponding anionic form.

In accordance with some variations of this embodiment of the invention, $Y^{x-}$ is of the formula $[R^1R^2N-A-COO]^{x-}$ or $[R^1R^2N-A-SO_3]^{x-}$, wherein:

A is a bond, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from $-COOH$, $-COH$, $-SCH_3$, $-NH_2$, $=NH$, $-NHC(=NH)NH_2$, $-C(=O)NH_2$, $-OH$, 4-hydroxyphenyl, 5-imidazolyl, 3-indolyl, halogen, $-SO_3H$, $=O$, $C_{1-8}$ alkyl, $C_{3-8}$ cycloalkyl, $C_{4-9}$ cycloalkylalkyl, phenyl, 4-methylphenyl, benzyl, $-O-C_{3-8}$ cyclalkyl, $-O-C_{3-8}$ cycloalkyl, $-O-C_{4-9}$ cycloalkylalkyl, $-O$-phenyl, $-O$-4-methylphenyl, $-O$-benzyl, $-SO_2R^7$ or $-NHR^7$ wherein $R^7$ is H, $C_{1-8}$ alkyl, phenyl, 4-methylphenyl, benzyl or $-NH_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

$R^1$ and $R^2$ are each independently selected from the group consisting of H, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from $-COOH$, $-COH$, $-SCH_3$, $-NH_2$, $=NH$, $-NHC(=NH)NH_2$, $-C(=O)NH_2$, $-OH$, 4-hydroxyphenyl, 5-imidazolyl, 3-indolyl, halogen, $-SO_3H$, $=O$, $C_{1-8}$ alkyl, $C_{3-8}$ cycloalkyl, $C_{4-9}$ cycloalkylalkyl, phenyl, 4-methylphenyl, benzyl, $-O-C_{3-8}$ cyclalkyl, $-O-C_{3-8}$ cycloalkyl, $-O-C_{4-9}$ cycloalkylalkyl, $-O$-phenyl, $-O$-4-methylphenyl, $-O$-benzyl, $-SO_2R^7$ or $-NHR^7$ wherein $R^7$ is H, $C_{1-8}$ alkyl, phenyl, 4-methylphenyl, benzyl or $-NH_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

or $R^1$ and A, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, $-OC_{1-6}$ alkyl or $-OC_{3-8}$ cycloalkyl;

or $R^1$ and $R^2$, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl.

In accordance with some variations of this embodiment of the invention, Y is of the formula $R^1R^2N$-A-COOH or $R^1R^2N$-A-$SO_3H$, wherein:

A is a bond, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_{4}$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —$SCH_3$, —$NH_2$, =NH, —NHC(=NH)$NH_2$, —C(=O)$NH_2$, —OH, 4-hydroxyphenyl, 5-imidazolyl, 3-indolyl, halogen, —$SO_3H$, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —$SO_2R^7$ or —$NHR^7$ wherein $R^7$ is H, $C_{1-8}$ alkyl, phenyl, 4-methylphenyl, benzyl or —$NH_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

$R^1$ and $R^2$ are each independently selected from the group consisting of H, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —$SCH_3$, —$NH_2$, =NH, —NHC(=NH)$NH_2$, —C(=O)$NH_2$, —OH, 4-hydroxyphenyl, 5-imidazolyl, 3-indolyl, halogen, —$SO_3H$, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —$SO_2R^7$ or —$NHR^7$ wherein $R^7$ is H, $C_{1-8}$ alkyl, phenyl, 4-methylphenyl, benzyl or —$NH_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

or $R^1$ and A, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl;

or $R^1$ and $R^2$, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl.

In some variations of this embodiment of the invention, the bromide and the nitrogen-containing compound are mixed to form a mixture of bromide and amine, which is diluted prior to mixing with the hypochlorite. In other variations on this embodiment of the invention, the bromide is diluted separately from the nitrogen-containing compound, and the bromide is diluted prior to mixing with the nitrogen-containing compound and the hypochlorite.

In some variations of this embodiment of the invention, the bromide is an alkali or alkaline earth metal bromide salt or a mixture of alkali or alkaline earth metal bromide salts. In some variations of this embodiment of the invention, the bromide is selected from the group consisting of HBr, LiBr, NaBr, KBr, $CaBr_2$ and $MgBr_2$ and mixtures thereof. In some variations of this embodiment of the invention, the bromide comprises a salt selected from the group consisting of sodium bromide and potassium bromide. In some variations of this embodiment of the invention, the bromide comprises or is NaBr.

In some variations of this embodiment of the invention, the bromide and nitrogen-containing compound are present in a molar ratio of between 20:1 and 1:10. In other variations of this embodiment of the invention, the bromide and nitrogen-containing compound are present in a molar ratio of between 2:1 and 1:2. In some variations of this embodiment of the invention, the bromide and nitrogen-containing compound are present in equimolar amounts. In some variations of this embodiment of the invention, the molar ratio of primary amine groups in the nitrogen-containing compound to the bromide is between 1:10 and 20:1. In other variations of this embodiment of the invention, the molar ratio of primary amine groups in the nitrogen-containing compound to the bromide in is between 1:2 and 2:1. In some variations of this embodiment of the invention, the molar ratio of primary amine groups in the nitrogen-containing compound to the bromide is 1:1. In some variations of this embodiment of the invention, the total amount of bromide and nitrogen-containing compound prior to dilution is between 10 and 40% w/v.

In accordance with some variations of this embodiment of the invention, the concentration of the hypochlorite oxidant in the aqueous hypochlorite oxidant solution immediately prior to mixing with the nitrogen-containing compound is not more than 24,000 ppm as total chlorine. In accordance with some variations of this embodiment of the invention, the concentration of the hypochlorite oxidant in the aqueous hypochlorite oxidant solution immediately prior to mixing with the nitrogen-containing compound is not more than 12,000 ppm as total chlorine.

In accordance with some variations of this embodiment of the invention, the nitrogen-containing compound or mixture thereof is in an aqueous solution at a concentration of 0.5-60% w/v prior to mixing with the hypochlorite oxidant solution.

In accordance with some variations of this embodiment of the invention, the mixing takes place in a mixing chamber into and out of which there is a continuous flow of water during the mixing.

In accordance with some variations of this embodiment of the invention, the biocide is applied to the medium substantially as the biocide is formed. In accordance with other variations of this embodiment of the invention, the biocide is applied to the medium within 30 seconds of formation of the biocide. In accordance with other variations of this embodiment of the invention, the biocide is applied to the medium within 60 seconds of formation of the biocide. In accordance with other variations of this embodiment of the invention, the biocide is applied to the medium within 90 seconds of formation of the biocide. In accordance with other variations of this embodiment of the invention, the biocide is applied to the medium within 120 seconds of formation of the biocide. In accordance with other variations of this embodiment of the invention, the biocide is applied to the medium within 150 seconds of formation of the biocide. In accordance with other variations of this embodiment of the invention, the biocide is applied to the medium within 180 seconds of formation of the biocide.

In accordance with some variations of this embodiment of the invention, the mixing chamber is a conduit.

In accordance with other variations of this embodiment of the invention, the mixing takes place in a mixing chamber out of which there is not a continuous flow of water during the mixing. In accordance with other variations of this embodiment of the invention, biocide is applied to the medium substantially immediately upon completion of the mixing. In accordance with other variations of this embodiment of the invention, the biocide is applied to the medium within 30 seconds of completion of the mixing. In accordance with other variations of this embodiment of the invention, the biocide is applied to the medium within 60 seconds of completion of the mixing. In accordance with other variations of this embodiment of the invention, the biocide is applied to the medium within 90 seconds of completion of the mixing. In accordance with other variations of this embodiment of the invention, the biocide is applied to the medium within 120 seconds of completion of the mixing. In accordance with other variations of this embodiment of the invention, the biocide is applied to the medium within 150 seconds of completion of the mixing. In accordance with other variations of this embodiment of the invention, the biocide is applied to the medium within 180 seconds of completion of the mixing.

In accordance with some variations of this embodiment of the invention, the hypochlorite oxidant is selected from the group consisting of alkaline and alkali earth metal hypochlorites, hypochlorite released to water from a stable chlorine carrier and hypochlorite formed in situ from chlorine gas, and mixtures thereof. In accordance with some variations of this embodiment of the invention, the stable chlorine carrier is selected from the group consisting of trichlorocyanuric acid, dichlorodimethylhydantoin and monochlorodimethylhydantoin. In accordance with some variations of this embodiment of the invention, the hypochlorite oxidant is selected from the group consisting of lithium hypochlorite, sodium hypochlorite, calcium hypochlorite, magnesium hypochlorite and potassium hypochlorite. In accordance with some variations of this embodiment of the invention, the hypochlorite oxidant is sodium hypochlorite.

In accordance with some variations of this embodiment of the invention, the nitrogen-containing compound is selected from the group consisting of carbamic acid, sulfamic acid, glycine, glutamine, arginine, histidine, lysine, and mixtures thereof.

In accordance with some variations of this embodiment of the invention, Y is selected from the group consisting of carbamic acid, sulfamic acid, glycine, glutamine, arginine, histidine, and lysine.

In accordance with some variations of this embodiment of the invention, the molar ratio of nitrogen atoms in the nitrogen-containing compound or mixture thereof to the hypochlorite oxidant is 1:1. In accordance with some variations of this embodiment of the invention, the molar ratio of the nitrogen-containing compound to the hypochlorite oxidant is 1:1. In accordance with some variations of this embodiment of the invention, the molar ratio of nitrogen atoms in the nitrogen-containing compound or mixture thereof to the hypochlorite oxidant is greater than 1:1. In accordance with other variations of this embodiment of the invention, the molar ratio of the nitrogen-containing compound to the hypochlorite oxidant is greater than 1:1.

In accordance with some variations of this embodiment of the invention, the concentration of the hypochlorite oxidant in the aqueous hypochlorite oxidant solution prior to mixing with the nitrogen-containing compound is not more than 24,000 ppm as total chlorine, and the mixing chamber comprises a conduit through which water flows as the hypochlorite oxidant solution and the nitrogen-containing compound are mixed. In accordance with some variations of this embodiment of the invention, the concentration of the hypochlorite oxidant in the aqueous hypochlorite oxidant solution immediately prior to mixing with the nitrogen-containing compound is not more than 12,000 ppm as total chlorine. In accordance with some variations of this embodiment of the invention, the solution of hypochlorite oxidant is prepared in situ in the conduit prior to addition of the solution of the nitrogen-containing compound to the conduit.

In accordance with some variations of this embodiment of the invention, the nitrogen-containing compound is diluted prior to mixing with the hypochlorite oxidant.

In accordance with some variations of this embodiment of the invention, the biocide has a pH of between 8.0 and 11.5 immediately prior to being applied to the medium. In accordance with some variations of this embodiment of the invention, the biocide has a pH of at least 8.5 immediately prior to being applied to the medium. In accordance with some variations of this embodiment of the invention, the biocide has a pH of at least 9.0 immediately prior to being applied to the medium. In accordance with some variations of this embodiment of the invention, the biocide has a pH of at least 9.5 immediately prior to being applied to the medium. In accordance with some variations of this embodiment of the invention, the biocide has a pH of at least 10.0 immediately prior to being applied to the medium. In accordance with some variations of this embodiment of the invention, the biocide has a pH of at least 10.5 immediately prior to being applied to the medium. In accordance with some variations of this embodiment of the invention, the biocide has a pH of at least 11.0 immediately prior to being applied to the medium. In accordance with some variations of this embodiment of the invention, the biocide has a pH of no more than 11.5 immediately prior to being applied to the medium.

In accordance with some variations of this embodiment of the invention, the medium is selected from the group consisting of pulp and paper factory process water, cooling tower water, waste water, reclaimed waste water, clay slurries, starch slurries, sludge, soil, colloidal suspensions, and irrigation water. In accordance with some variations of this embodiment of the invention, the medium is pulp and paper factory water. In accordance with some variations of this embodiment of the invention, the medium is cooling tower water. In accordance with some variations of this embodiment of the invention, the medium is waste water. In accordance with some variations of this embodiment of the invention, the medium is reclaimed waste water. In accordance with some variations of this embodiment of the invention, the medium is a clay slurry. In accordance with some variations of this embodiment of the invention, the medium is a starch slurry. In accordance with some variations of this embodiment of the invention, the medium is a sludge. In accordance with some variations of this embodiment of the invention, the medium is soil. In accordance with some variations of this embodiment of the invention, the medium is a colloidal suspension. In accordance with some variations of this embodiment of the invention, the medium is irrigation water. In accordance with some variations of this embodiment of the invention, the medium is a medium containing strong reducing agents or having a high reducing capacity, viz. an ORP of not greater than 150 millivolts.

In accordance with some variations of this embodiment of the invention, the biocide is applied to the medium periodically with a duty cycle of less than 1:2. In accordance with some variations of this embodiment of the invention, the biocide is applied to the medium periodically with a duty cycle of between about 1:5 and 1:10. In accordance with some variations of this embodiment of the invention, the biocide is applied to the medium periodically with a duty cycle of less than 1:10. In accordance with some variations of this embodiment of the invention, the biocide is applied to the medium periodically with a duty cycle of less than 1:25. In accordance with some variations of this embodiment of the invention, the biocide is applied to the medium periodically with a duty cycle of less than 1:50.

In accordance with some variations of this embodiment of the invention, the biocide is applied to the medium at a rate to maintain in the biocide a stable pH of at least 8.0 as the biocide is produced.

In accordance with some variations of this embodiment of the invention, the concentration of the biocide immediately prior to being applied to the medium is from 1000 to 12,000 ppm expressed as total chlorine.

In accordance with some variations of this embodiment of the invention, the medium has a pH of between about 5 and about 11.5 before the biocide is applied to the medium. In accordance with some variations of this embodiment of the invention, the medium has a pH of between about 6 and about 10 before the biocide is applied to the medium. In accordance with some variations of this embodiment of the invention, the medium has a pH of between about 7 and about 9 before the biocide is applied to the medium.

In accordance with some variations of this embodiment of the invention, the concentration of the biocide in the medium, upon application of the biocide to the medium, is 0.5-300 ppm expressed as chlorine. In accordance with some variations of this embodiment of the invention, the concentration of the biocide in the medium, upon application of the biocide to the medium, is 1-10 ppm expressed as chlorine.

In accordance with some variations of this embodiment of the invention, the biocide is effective within 24 hours of application to the medium. In accordance with some variations of this embodiment of the invention, the biocide is effective within 1 hour of application to the medium. In accordance with some variations of this embodiment of the invention, the biocide is effective within 20 minutes of application to the medium. In accordance with some variations of this embodiment of the invention, the biocide is effective within 15 minutes of application to the medium.

In accordance with some variations of this embodiment of the invention, the biocide is capable of reducing microbial activity by at least 50% within 3 hours after administration. In accordance with some variations of this embodiment of the invention, the biocide is capable of reducing microbial activity by at least 50% within 1 hour after administration. In accordance with some variations of this embodiment of the invention, the biocide is capable of reducing microbial activity by at least 50% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of reducing microbial activity by at least 75% within 3 hours after administration. In accordance with some variations of this embodiment of the invention, the biocide is capable of reducing microbial activity by at least 75% within 1 hour after administration. In accordance with some variations of this embodiment of the invention, the biocide is capable of reducing microbial activity by at least 75% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of reducing microbial activity by at least 90% within 3 hours after administration. In accordance with some variations of this embodiment of the invention, the biocide is capable of reducing microbial activity by at least 90% within 1 hour after administration. In accordance with some variations of this embodiment of the invention, the biocide is capable of reducing microbial activity by at least 90% within 30 minutes after administration. In the context of these variations of this embodiment of the invention, reduction in microbial activity may be correlated to an increase in operational efficiency of the system being treated. For example, in a paper machine, a reduction in microbial activity will result in improved runnability of the paper machine. In some contexts, reduced microbial activity can be correlated to decreased production of ATP or to decreased production of catalase. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured. In accordance with some variations of this embodiment of the invention, the reduction of microbial activity is measured in a test sample. In accordance with some variations of this embodiment of the invention, the reduction of microbial activity is measured on site.

In accordance with some variations of this embodiment of the invention, the biocide is capable of killing at least 50% of the microorganisms in a liquid test sample within 3 hours after administration. In accordance with some variations of this embodiment of the invention, the biocide is capable of killing at least 50% of the microorganisms in a liquid test sample within 1 hour after administration. In accordance with some variations of this embodiment of the invention, the biocide is capable of killing at least 50% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the biocide is capable of killing at least 75% of the microorganisms in a liquid test sample within 3 hours after administration. In accordance with some variations of this embodiment of the invention, the biocide is capable of killing at least 75% of the microorganisms in a liquid test sample within 1 hour after administration. In accordance with some variations of this embodiment of the invention, the biocide is capable of killing at least 75% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the biocide is capable of killing at least 90% of the microorganisms in a liquid test sample within 3 hours after administration. In accordance with some variations of this embodiment of the invention, the biocide is capable of killing at least 90% of the microorganisms in a liquid test sample within 1 hour after administration. In accordance with some variations of this embodiment of the invention, the biocide is capable of killing at least 90% of the microorganisms in a liquid test sample within 30 minutes after administration. In accordance with some variations of this embodiment of the invention, after the recited time period there is a residual of biocide, expressed as total chlorine, of at least 0.5 ppm. In accordance with some variations of this embodiment of the invention, after the recited time period there is a residual of biocide, expressed as total chlorine, that is too low to be measured.

In accordance with some variations of this embodiment of the invention, the medium is present in a system from which a portion of the medium is discharged and replaced during the regular course of operation of the system. In accordance with some variations of this embodiment of the invention, the portion of the medium which is discharged and replaced during the regular course of operation of the system is continuously discharged and replaced during the regular course of operation of the system. In accordance with some variations of this embodiment of the invention, the portion of the medium which is discharged and replaced during the regular course of operation of the system is discharged and replaced at least once every 24 hours during the regular course of operation of the system.

There is also provided, in accordance with an embodiment of the invention, an apparatus for introducing a biocide into a medium, comprising:

a nitrogen-containing compound containing reservoir containing a nitrogen-containing compound which is selected from the group consisting of salts of the formula $Y^{x-}[NH_2R^3R^4]^+_x$, salts of the formula $Y^{x-}Z^{n+}_{x/n}$, and molecules Y per se, wherein Y, $R^3$, $R^4$, x, Z and n are as defined above;

a source of hypochlorite oxidant dilution having a concentration of not more than 24,000 ppm as total chlorine;

a source of bromide dilution;

and a mixing chamber operable to mix the hypochlorite dilution, the bromide dilution and the nitrogen-containing compound in a molar ratio of nitrogen atoms in the nitrogen-containing compound to hypochlorite of at least 1:1, to produce the biocide in the mixing chamber.

In some variations of this embodiment of the invention, the source of hypochlorite oxidant dilution has a concentration of not more than 12,000 ppm as total chlorine.

In some variations of this embodiment of the invention, Y is selected from the group consisting of straight, branched and cyclic molecules containing at least one moiety selected from the group consisting of an amide moiety, an imide moiety, a sulfamide moiety, a sulfamide moiety, and an amineimine moiety, and $Y^{x-}$ is basic form of the molecule. In some variations of this embodiment of the invention, at least one of the at least one amide moiety, imide moiety, sulfamide moiety, sulfamide moiety, or amineimine moiety is ionized to the corresponding anionic form.

In some variations of this embodiment of the invention, Y is an amphoteric molecule containing at least one moiety selected from the group consisting of COOH and $SO_3H$ and at least one moiety selected from the group consisting of a primary amine moiety, a secondary amine moiety, and a tertiary amine moiety, and $Y^{x-}$ is an anionic form of the amphoteric molecule. In some variations of this embodiment of the invention, at least one of the at least one COOH and $SO_3H$ is ionized to the corresponding anionic form.

In some variations of this embodiment of the invention, Q is an amphoteric molecule containing at least one moiety selected from the group consisting of COOH and $SO_3H$ and at least one moiety selected from the group consisting of a primary amine moiety, a secondary amine moiety, and a tertiary amine moiety, and $Y^{x-}$ is an anionic form of the amphoteric molecule.

In accordance with some variations of this embodiment of the invention, the source of hypochlorite oxidant dilution comprises a hypochlorite-containing reservoir containing a hypochlorite oxidant solution, and a diluter operable to dilute the hypochlorite oxidant solution to produce the hypochlorite oxidant dilution having a concentration of not more than 24,000 ppm expressed as total chlorine. In accordance with some variations of this embodiment of the invention, the diluter is operable to dilute the hypochlorite oxidant solution to produce the hypochlorite oxidant dilution having a concentration of not more than 12,000 ppm as total chlorine. In accordance with some variations of this embodiment of the invention, the diluter and the mixing chamber are a single conduit which is adapted to dilute the hypochlorite oxidant prior to mixing with the salt or mixture of salts.

In accordance with some variations of this embodiment of the invention, the nitrogen-containing compound is present in the nitrogen-compound containing reservoir as an aqueous solution.

In accordance with some variations of this embodiment of the invention, the bromide is present in the nitrogen-containing compound containing reservoir. In accordance with some variations of this embodiment of the invention, the bromide is present in a separate reservoir.

In accordance with some variations of this embodiment of the invention, the source of bromide dilution comprises a bromide-containing reservoir containing a bromide solution, and a diluter operable to dilute the bromide solution to produce the bromide dilution. In accordance with some variations of this embodiment of the invention, the diluter which the dilutes the bromide and the diluter which dilutes the oxidant and the mixing chamber are a single conduit which is adapted to dilute the hypochlorite oxidant prior to mixing with the nitrogen-containing compound and prior to mixing with the bromide.

In accordance with some variations of this embodiment of the invention, the molar ratio of nitrogen atoms in the nitrogen-containing compound or mixture thereof to the hypochlorite oxidant is 1:1. In accordance with some variations of this embodiment of the invention, the molar ratio of the nitrogen-containing compound to the hypochlorite oxidant is 1:1. In accordance with some variations of this embodiment of the invention, the molar ratio of nitrogen atoms in the nitrogen-containing compound or mixture thereof to the hypochlorite oxidant is greater than 1:1. In accordance with other variations of this embodiment of the invention, the molar ratio of the nitrogen-containing compound to the hypochlorite oxidant is greater than 1:1.

In some variations of this embodiment of the invention, the bromide and nitrogen-containing compound are present in a molar ratio of between 20:1 and 1:10. In other variations of this embodiment of the invention, the bromide and nitrogen-containing compound are present in a molar ratio of between 2:1 and 1:2. In some variations of this embodiment of the invention, the bromide and nitrogen-containing compound are present in equimolar amounts. In some variations of this embodiment of the invention, the molar ratio of primary amine groups in the nitrogen-containing compound to the bromide is between 1:10 and 20:1. In other variations of this embodiment of the invention, the molar ratio of primary amine groups in the nitrogen-containing compound to the bromide in is between 1:2 and 2:1. In some variations of this embodiment of the invention, the molar ratio of primary amine groups in the nitrogen-containing compound to the bromide is 1:1. In some variations of this embodiment of the invention, the total amount of bromide and nitrogen-containing compound prior to dilution is between 10 and 40% w/v.

In accordance with some variations of this embodiment of the invention, the system further comprises an egress adapted to enable introduction of the biocide from the mixing vessel into the medium.

BRIEF DESCRIPTION OF THE DRAWINGS

Embodiments of the invention are more particularly described with respect to a number of examples set forth below, and also with respect to the accompanying drawings wherein.

Figure 1:
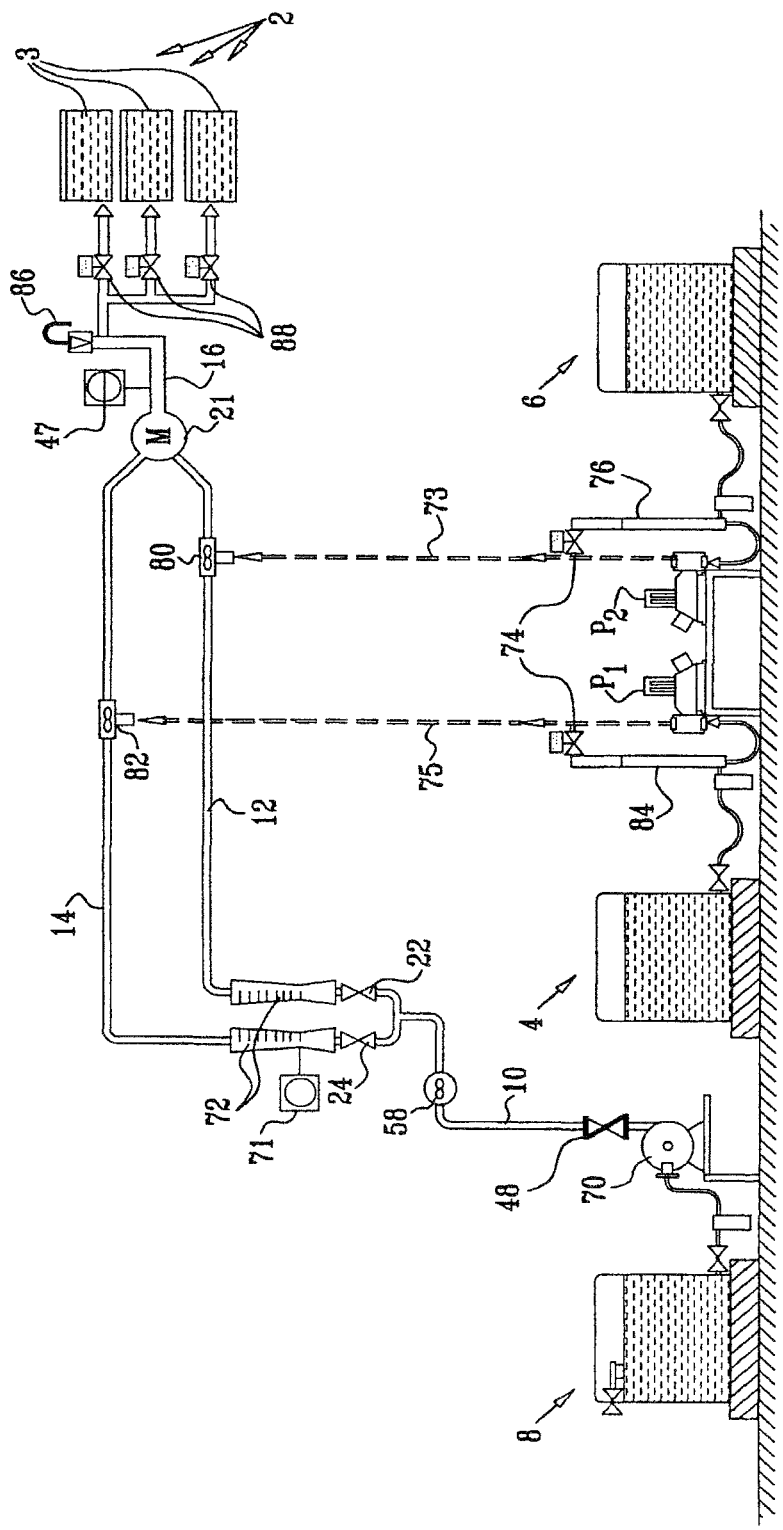
FIG. 1 depicts an apparatus constructed and operative to enable the practice of embodiments of the present invention.

The apparatus illustrated in FIG. 1 produces a biocide that is introduced into or applied to a medium 3, such as water, at one or more locations 2. In some embodiments of the invention, the biocide is formed by mixing a hypochlorite oxidant and a salt of a nitrogen-containing compound that contains at least one moiety selected from the group consisting of a primary amine moiety, a secondary amine moiety, a tertiary amine moiety, an amide moiety, an imide moiety, a sulfamide moiety, a sulfimide moiety, and an amineimine moiety, or a mixture of such salts. In some embodiments of the invention, the salt is of the formula $Y^{x-}[NH_2R^3R^4]^+_x$, wherein $Y^{x-}$ is a basic form of an acid Y that contains at least one moiety selected from the group consisting of a primary amine moiety, a secondary amine moiety, a tertiary amine moiety, an amide moiety, an imide moiety, a sulfamide moiety, a sulfimide moiety, and an amineimine moiety; and $[NH_2R^3R^4]^+$ is an acidic form of a base $NHR^3R^4$ wherein:
$R^3$ and $R^4$ are each independently selected from the group consisting of H and $C_{1-8}$ alkyl, or $R^3$ and $R^4$, together with the nitrogen atom to which they are attached, form a 5- to 10-member heterocyclic ring optionally substituted by one or more groups selected from $C_{1-6}$ alkyl, $C_{3-8}$ cycloalkyl, halogen, hydroxy, —$OC_{1-6}$ alkyl or —$OC_{3-8}$ cycloalkyl; and x is 1 to 3.

In some embodiments of the invention, Y is selected from the group consisting of straight, branched and cyclic molecules containing at least one moiety selected from the group consisting of an amide moiety, an imide moiety, a sulfamide moiety, a sulfimide moiety, and an amineimine moiety. In some of these embodiments of the invention, $Y^{x-}$ is a basic form of Y. In some of these embodiments of the invention, at least one of the at least one amide moiety, imide moiety, sulfamide moiety, sulfimide moiety, or amineimine moiety is ionized to the corresponding anionic form.

In some embodiments of the invention, Y is selected from the group consisting of amphoteric molecules containing at least one moiety selected from the group consisting of a primary amine moiety, a secondary amine moiety, and a tertiary amine moiety, and at least one moiety selected from the group consisting of COOH and $SO_3H$. In some of these embodiments of the invention, $Y^{x-}$ is an anionic form of the amphoteric molecule. In some of these embodiments of the invention, at least one of the at least one COOH and $SO_3H$ is ionized to the corresponding anionic form. In some embodiments of the invention, $Y^{x-}$ is of the formula $[R^1R^2N-A-COO]^{x-}$ or $[R^1R^2N-A-SO_3]^{x-}$, wherein:

A is a bond, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —$SCH_3$, —$NH_2$, =NH, —NHC(=NH)$NH_2$, —C(=O)$NH_2$, —OH, 4-hydroxyphenyl, 5-imidazolyl, 3-indolyl, halogen, —$SO_3H$, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —$SO_2R^7$ or —$NHR^7$ wherein $R^7$ is H, $C_{1-8}$ alkyl, phenyl, 4-methylphenyl, benzyl or —$NH_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

$R^1$ and $R^2$ are each independently selected from the group consisting of H, straight-chain or branched $C_{1-20}$ alkyl, straight-chain or branched $C_{2-20}$ alkenyl, straight-chain or branched $C_{2-20}$ alkynyl, $C_{3-10}$ cycloalkyl, straight-chain or branched $C_4$-$C_{20}$ alkylcycloalkyl, $C_{4-10}$ cycloalkenyl, $C_{4-10}$ cycloalkynyl, or $C_6$-$C_{10}$ aryl, wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl is optionally substituted with one or more groups selected from —COOH, —COH, —SCH$_3$, —NH$_2$, =NH, —NHC(=NH)NH$_2$, —C(=O)NH$_2$, —OH, 4-hydroxyphenyl, 5-imidazolyl, 3-indolyl, halogen, —SO$_3$H, =O, $C_{1-8}$ alkyl, $C_{3-8}$ cycloalkyl, $C_{4-9}$ cycloalkylalkyl, phenyl, 4-methylphenyl, benzyl, —O—$C_{3-8}$ cyclalkyl, —O—$C_{3-8}$ cycloalkyl, —O—$C_{4-9}$ cycloalkylalkyl, —O-phenyl, —O-4-methylphenyl, —O-benzyl, —SO$_2$R$^7$ or —NHR$^7$ wherein R$^7$ is H, $C_{1-8}$ alkyl, phenyl, 4-methylphenyl, benzyl or —NH$_2$, and wherein each $C_{1-20}$ alkyl, $C_{2-20}$ alkenyl, $C_{2-20}$ alkynyl, $C_{3-10}$ cycloalkyl, $C_4$-$C_{20}$ alkylcycloalkyl, $C_{4-10}$ cycloalkenyl, $C_{4-10}$ cycloalkynyl or $C_6$-$C_{10}$ aryl optionally contains one to three heteroatoms selected from N, O and S;

or $R^1$ and A, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —OC$_{1-6}$ alkyl or —OC$_{3-8}$ cycloalkyl;

or $R^1$ and $R^2$, together with the nitrogen atom to which they are attached, form a 5- to 10-member heterocyclic ring or a 5- to 10-member heteroaromatic ring in which the free electron pair of the nitrogen atom to which $R^1$ and A is attached is not part of the aromatic pi-electron system, the 5- to 10-member heterocyclic or heteroaromatic ring being optionally substituted by one or more groups selected from $C_{1-6}$ alkyl, $C_{3-8}$ cycloalkyl, halogen, hydroxy, —OC$_{1-6}$ alkyl or —OC$_{3-8}$ cycloalkyl.

In other embodiments of the invention, the salt is of the form $Y^{x-}Z^{n+}{}_{x/n}$, wherein $Y^{x-}$ is as defined above, and $Z^{n+}$ is a cation other than a cation of the form $[NH_2R^3R^4]^+$ as defined above, and n is a whole number greater than zero.

In other embodiments of the invention, the hypochlorite is mixed with a nitrogen containing compound which is not a salt but is a compound Y per se as defined above, provided that the compound Y is not sulfamic acid, melamine, cyanuric acid, hydantoin, dialkyl hydantoin such as dimethyl hydantoin, biuret, succinamide, succinimide, creatine, or creatinine As will be explained hereinbelow, in some embodiments of the invention, in forming the biocide the hypochlorite and nitrogen-containing compound or salt thereof are also mixed with a bromide.

In FIG. 1, reservoir 4 contains a solution of hypochlorite, and reservoir 6 contains a solution of the nitrogen-containing compound or salt thereof. In some embodiments of the invention, the solution contained in reservoir 6 also comprises bromide.

As shown in FIG. 1, water is fed from a source 8, shown in FIG. 1 as a reservoir 8 from which water is pumped by pump 70, via a water pipe 10 through parallel flow meters 72 and into a corresponding pair of branch lines 12, 14, which connect to a mixer 21 which feeds common outlet pipe 16 leading to medium 3 at the locations 2. A low-water flow switch 71 is operably connected to the flow indicator 72 of line 12. Outlet pipe 16 is equipped with a siphon breaker 86, and may also be equipped with a pH meter 47 to monitor the pH of the biocide.

Pumps $P_1$ and $P_2$, which may be for example pusaltile pumps, peristaltic pumps, other types of pumps or the equivalents of pumps (such as venturis) as are known in the art, pump the hypochlorite and nitrogen-containing compound or salt thereof from reservoirs 4 and 6 respectively through lines 75 and 73 respectively into lines 14 and 12 at junction pieces 82 and 80, respectively. These junction pieces may be, for example, simple T-connectors, or they may be designed to facilitate mixing of the solutions from reservoirs 4 and 6 with the water flowing through lines 14 and 12. Between reservoirs 6 and 4 are calibration tubes 76 and 84 and valves 74.

Thus, depending on the concentration of the components in reservoirs 4 and 6, the rate at which these components are pumped into lines 14 and 12 respectively, and the rate of flow of water through lines 12 and 14, the hypochlorite oxidant and nitrogen-containing compound or salt thereof may be diluted and mixed in desired proportions. The reaction product, namely the biocide produced by the reaction of the hypochlorite and nitrogen-containing compound or salt thereof, may thus be applied directly from outlet pipe 16 into the medium 3, within a brief time after the formation of the biocide. In alternative embodiments of the invention (not shown), mixer 21 is replaced by a ingress chamber or a junction piece, in which case the dilutions mix and react as they flow through outlet pipe 16, so that by the time the fluid flowing through outlet pipe 16 is introduced into the liquid 3, the biocide has been produced. In these alternative embodiments of the invention, outlet pipe 16 rather than mixer 21 functions as a mixing chamber.

It will also be appreciated that although as depicted in FIG. 1, the solution of nitrogen-containing compound or salt thereof is diluted prior to mixing with the hypochlorite oxidant dilution, in those embodiments of the invention in which bromide is not employed, this solution need not be diluted prior to mixing with the hypochlorite dilution. Irrespective of whether the nitrogen-containing compound or salt thereof is diluted or not before mixing with the hypochlorite, the nitrogen-containing compound or salt thereof should be mixed with the hypochlorite oxidant in equimolar amounts or in a molar excess relative to the hypochlorite oxidant. It will also be appreciated that in some embodiments, the concentration of hypochlorite immediately prior to mixing with the nitrogen-containing compound or salt thereof does not exceed 24,000 ppm expressed as total chlorine, and that in some embodiments, the concentration of biocide prior to application to the medium does not exceed 12,000 ppm expressed as total chlorine.

Irrespective whether or not a mixer 21 is utilized, the flow through outlet pipe 16 should be sufficiently fast that the biocide does not have time to decompose prior to introduction into the medium 3. In many embodiments of the invention, the time from which the diluted oxidant, nitrogen-containing compound or salt thereof, and if present, diluted bromide are mixed with each other to form the biocide until the biocide is injected from pipe 16 into medium 3 is three minutes or less. In some embodiments, the time is two-and-a-half minutes or less, in some embodiments the time is two minutes or less, in some embodiments the time is one-and-a-half minutes or less, in some embodiments the time is one minute or less, and in some embodiments the time is 30 seconds or less. In other embodiments of the invention in which the biocide is stable for more than a few minutes, the biocide may be stored (e.g. in a reservoir, not shown) prior to application to the medium.

The two branch lines 12, 14 include control valves 22, 24, which enable the flow rate of the water through lines 12 and 14 to be controlled.

The control of the foregoing valves and pumps may be done by a control system (not shown). Outlet line 16, therefore, may also include a pH sensor 47 for sensing the pH of the biocide, which may give feedback to the control system to enable control of biocide production in response thereto. The control system may control the supply of the water from source 8 via an electrical valve 48. The apparatus may also be configured with alarms or other signalling devices, such as flow switch 71, which may give feedback to the control system. The illustrated system may further include a timer (not shown) which is pre-settable to fix both the lengths of time for which the biocide is to be fed via the outlet line 16 to the medium to be treated, as well as the time intervals between such feedings of the biocide. The control system may also be operative to control the operation of mixer 21.

The water supply line 10 from the water source 8 to the two branch lines 12, 14, may include additional control devices, such as a flow meter 58 for indicating the flow rate or flow volume.

As indicated earlier, the solution in reservoir 4 comprises a hypochlorite oxidant, and the solution within reservoir 6 comprises at least one nitrogen-containing compound or salt thereof and, in some embodiments of the invention, bromide. When present, the bromide may be provided in any suitable form. In some embodiments of the invention, the bromide is provided as an alkali or alkaline earth metal bromide salt, such as lithium bromide, sodium bromide, potassium bromide, calcium bromide, magnesium bromide or hydrobromic acid.

The oxidant may be chosen from alkali and alkaline earth metal hypochlorites, e.g. lithium hypochlorite, sodium hypochlorite, potassium hypochlorite, calcium hypchlorite or magnesium hypochlorite.

In some embodiments of the invention, the biocide has a pH of at least 8.0 immediately prior to its application to medium 3. In some embodiments of the invention, the biocide has a pH of at least 9.5 immediately prior to its application to medium 3. In some embodiments of the invention, the biocide has a pH of at least 10.0 immediately prior to its injection into medium 3. In some embodiments of the invention, the biocide has a pH of at least 10.5 immediately prior to its application to medium 3. In some embodiments of the invention, the biocide has a pH of at least 11.0 immediately prior to its application to medium 3. In some embodiments of the invention, the biocide has a pH of not more than 11.5 immediately prior to its application to medium 3. In an embodiment of the invention, the biocide is applied at a rate to maintain in the biocide a stable pH of at least 8.0 as it is produced.

Figure 2:
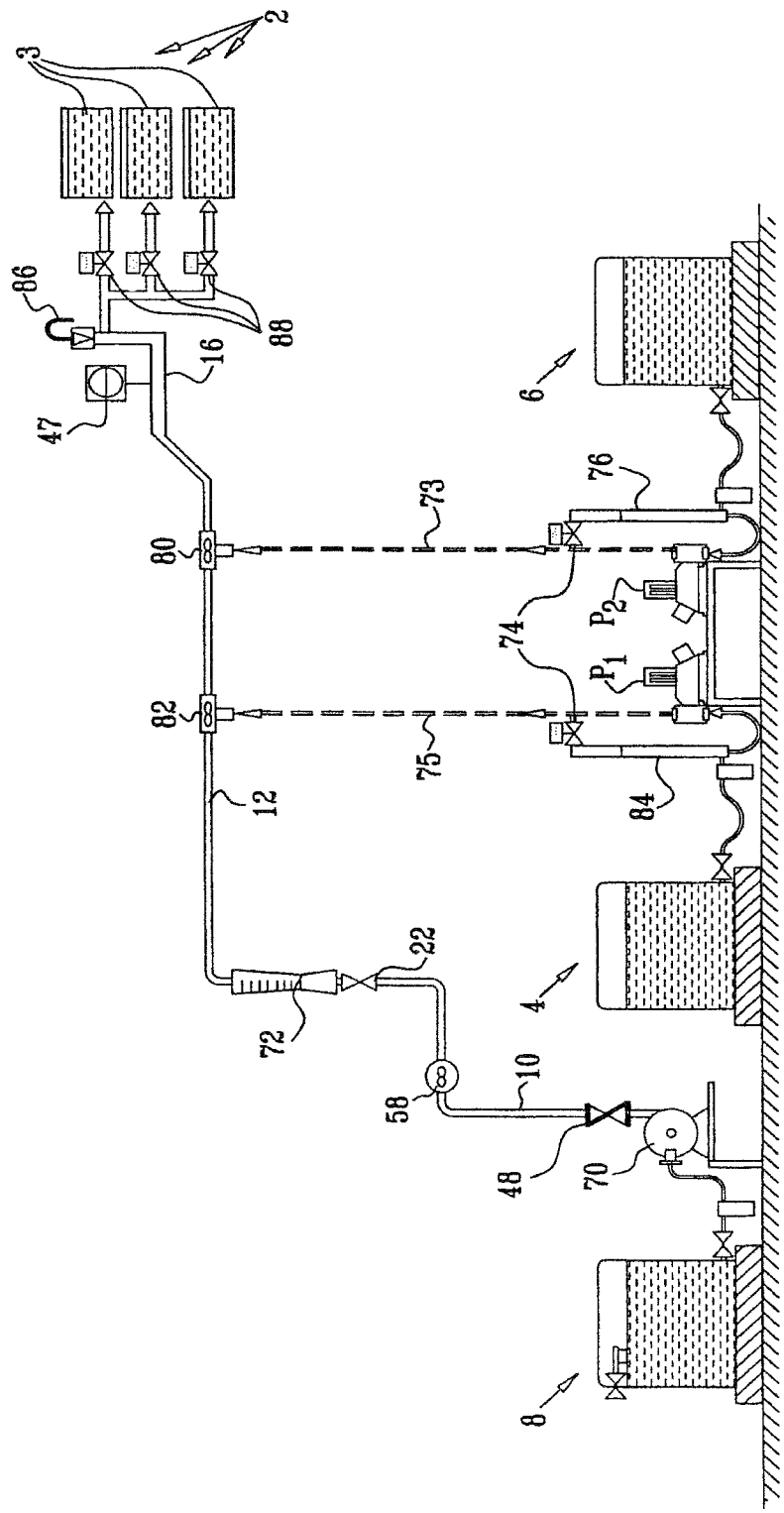
FIG. 2 depicts another apparatus constructed and operative to enable the practice of embodiments of the present invention.

FIG. 2 is similar to FIG. 1, with like numbers denoting elements of the system of FIG. 2 which are the same as in the system of FIG. 1 and which operate in the same way. In FIG. 2, only a single flow line 12 is used, and no mixer 21 is present. The solution from reservoir 4 is introduced into line 12 upstream of where the solution from reservoir 6 is introduced into the flow line. In this arrangement, the dilution of the nitrogen-containing compound or salt thereof, with or without bromide, may form in the presence of the oxidant dilution, as long as the molar ratio of nitrogen-containing compound or salt thereof to hypochlorite oxidant is at least 1:1. The dilutions mix as they flow through line 12 and out through pipe 16, which as shown in FIG. 2 constitutes a continuation of line 12.

In variations of what is depicted in FIG. 1, bromide may be diluted and introduced into mixer 21 separately from the nitrogen-containing compound. In variations of what is depicted in FIG. 2, bromide may be introduced to line 12 separately from the nitrogen-containing compound, provided that the bromide not introduced into line 12 upstream of where the nitrogen-containing is introduced into line 12.

It will be appreciated that in embodiments of the invention shown herein, the hypochlorite oxidant is diluted prior to mixing with the nitrogen-containing compound or salt thereof In the context of this patent application, the term "effective", when used in reference to a biocide, means that the biocide is capable of controlling microbial growth, as evidenced by the ability to kill at least 50% of the microorganism in a liquid test sample within 3 hours after administration, with a residual of biocide, expressed as total chlorine, of at least 0.5 ppm.

In the present application, the term "duty cycle" will be understood to mean the ratio between (a) the amount of time a biocide is administered to the water to be treated and (b) the amount of time the biocide is not administered to the water to be treated.

It will also be appreciated that in the context of biofilm control, in embodiments of the invention it may not be necessary to kill microorganisms within the biofilm in order to control the biofilm, and that biofilm control in such cases can be adduced from direct observation of reduction of the presence of biofilm, or from observation of, for example, reduced production of ATP, reduced production of catalase, or other measurable variables which can be correlated with biofilm control or improved operational efficiency of the system being treated.

The present invention will be better understood through the following illustrative and non-limitative examples of embodiments thereof.

EXPERIMENTAL

Series 1

General: Tests were conducted in an aqueous test system consisting in each instance of deionized (DI) water to which starch (~7.5 g/l), calcium hydroxide (94 ppm), and sodium bicarbonate (1320 ppm) was added; pH was adjusted to 8.17 using hydrochloric acid. A suspension of microorganisms was prepared from a sample of pink slime removed from the surface of a paper machine. Microorganisms (MOs) were grown at 37° C.

As controls, in each test (a) biocide was added to DI water only, and (b) a sample of medium was left untreated by biocide.

In the following examples, biocides in accordance with embodiments of the present invention were prepared by simulating production of the biocides as described above. An appropriate volume of the solution containing the biocide was added to each test container, taking into account the final desired concentration of the biocide after addition to the test container. The decomposition rate of the biocidal active ingredient was monitored in the examples below by measuring the residue of total chlorine in the concentrate.

Example 1

Oxidation Reduction Potential (ORP)

Using an ORP electrode (WTW), oxidation-reduction potentials were measured in accordance with G. Degramont, "Water Treatment Handbook", Springer-Verlag, 1991, pp. 249-250, the contents of which are incorporated herein by reference.

In this example, four tests were conducted:

Test 1: In accordance with U.S. Pat. No. 6,478,972 ("Shim"), sodium sulfamate (14.62 g sulfamic acid dissolved in 100 ml DI water containing 7.2 g NaOH) and sodium hypochlorite (10.5% w/v expressed as $Cl_2$, commercial solution) were mixed (molar ratio of sulfamate to $Cl_2$ 1.007:1) to produce what Shim terms a "stabilized hypochlorite solution". The resulting mixture was immediately added to each of the aqueous test systems, in defined volumes to maintain feed levels of 4.2, 8.4 and 12.6 ppm (expressed as total chlorine) respectively.

Test 2: In accordance with Shim, sodium sulfamate (14.62 g sulfamic acid dissolved in 100 ml DI water containing 7.2 g NaOH) and sodium hypochlorite (10.5% w/v expressed as $Cl_2$, commercial solution) were mixed (molar ratio of sulfamate to $Cl_2$ 1.007:1) to produce what Shim terms is a "stabilized hypochlorite solution". Sodium bromide (15.5% w/v) (molar ratio of $Br^-$ to $Cl_2$ 1.014:1) was mixed into the "stabilized hypochlorite solution". A slight color change was noted as soon as NaBr was added to the "stabilized hypochlorite concentrate". An appropriate volume of the resulting mixture was immediately added to each of the aqueous test systems, in defined volumes to maintain feed levels of 4.2, 8.4 and 12.6 ppm (expressed as total chlorine) respectively.

Test 3: In accordance with Shim, sodium sulfamate (14.62 g sulfamic acid dissolved in 100 ml DI water) and sodium hypochlorite (10.5% w/v expressed as $Cl_2$, commercial solution) were mixed (molar ratio of sulfamic acid to $Cl_2$ 1.007:1) to produce what Shim terms a "stabilized hypochlorite solution". Sodium bromide (15.5% w/v) was mixed into the "stabilized hypochlorite solution" (molar ratio of $Br^-$ to $Cl_2$ 1.014:1) A significant color change was noted as soon as NaBr was added to the "stabilized hypochlorite solution". The resulting mixture was immediately added to each of the aqueous test systems, in defined volumes to maintain feed levels of 4.2, 8.4, and 12.6 ppm (expressed as total chlorine) respectively.

Test 4: In accordance with Shim, sulfamic acid (14.62 g in 100 ml DI water) and sodium hypochlorite (10.5% w/v expressed as $Cl_2$, commercial solution) were mixed. The mixture was immediately added to each of the aqueous test systems, in defined volumes to maintain feed levels of 4.2, 8.4 and 12.6 ppm (expressed as total chlorine) respectively. NaBr (15.5% w/v, molar ratio of $Br^-$ to $Cl_2$ 1.014:1) was simultaneously added separately to the aqueous system.

In tests 2, 3 and 4, ORP was measured two hours after the biocide was added to the aqueous system. The results are presented in Table 1, where ppm refers to the biocide feed level, expressed as $Cl_2$:

TABLE 1

| Treatment | ORP (millivolts) | | |
|---|---|---|---|
| | test 4 | test 2 | test 3 |
| 8.4 ppm, DI only | 340 | 405 | 420 |
| 4.2 ppm | 238 | 310 | 348 |
| 8.4 ppm | 231 | 294 | 330 |
| 12.6 ppm | 250 | 284 | 295 |
| 0 ppm | 200 | 200 | 200 |

The results in Table 1 show that the order and mode of addition of the chemicals in the method of Shim is significant, as is the identity of the chemicals.

Example 2

Residual Total Chlorine

Residual total chlorine in the aqueous system was measured 10 minutes and 24 hours after addition of biocide, using the DPD colorimetric method (see "Standard Methods for Examination of Waste and Waste Water", $17^{th}$ Edition (1989), pp. 4-62 to 4-64, the contents of which are incorporated herein by reference). As is known in the art, the rate of degradation of an oxidizer in an aqueous system is system-specific, i.e. the degradation rate of a given oxidizer is reproducible in a given aqueous system.

Test 4 is the same Test 4 conducted in Example 1.

Test 5: In accordance with an embodiment of the present invention, sodium sulfamate (14.62 g sulfamic acid dissolved in 100 ml DI water containing 7.2 g NaOH) was mixed with NaBr (15.5 g in 100 ml DI water) (sodium sulfamate and NaBr both equimolar to sodium hypochlorite) and diluted in DI water. Sodium hypochlorite (10.5% w/v, expressed as $Cl_2$) was diluted in DI water (to a concentration of 4200 ppm, 0.42% w/v expressed as $Cl_2$, equimolar to sulfamate and to bromide ion). The two diluted solutions were mixed according to the procedure described above. The biocide was immediately added to the aqueous system at a feed level of 2.1, 4.2 and 6.3 ppm expressed as total chlorine. The results are presented in Table 2 (presented as total chlorine as percent of feed).

TABLE 2

| | Total $Cl_2$ (as % of feed) | | | |
|---|---|---|---|---|
| treatment | test 4-10 min | test 4-24 hours | test 5-10 min | test 5-24 hours |
| 8.4 ppm, DI | 48.8 | 53.6 | | |
| 4.2 ppm, DI | | | 119.05 | 107.1 |
| 2.1 ppm | | | 42.86 | 2.4 |
| 4.2 ppm | 31 | 19.05 | 57.14 | 50 |
| 6.3 ppm | | | 71.4 | 57.1 |
| 8.4 ppm | 29.8 | 27.4 | | |
| 12.6 ppm | 39.7 | 34.1 | | |

*In the control samples in which biocide treatment was 0 ppm, the total $Cl_2$ was 0 ppm after both 10 minutes and 24 hours.

These results show that biocide formed according to Shim et al. is different than biocide formed in accordance with an embodiment of the present invention.

Example 3

Adenosine triphosphate (ATP) Concentration

ATP levels serve as a measure for the biochemical activity of microorganisms, and as such serve as a good model for the viability of a microbial culture after it has been exposed to a biocide. Thus, in the aqueous system of Tests 4 and 5 described above, the concentration of ATP was measured 20 minutes after the addition of the biocide. The results are presented in Table 3.

TABLE 3

| treatment | test 4 ATP (ng/ml) | test 5 ATP (ng/ml) |
|---|---|---|
| 2.1 ppm | | 0.58 |
| 4.2 ppm | 0.75 | 0.53 |
| 6.3 ppm | | 0.44 |

TABLE 3-continued

| treatment | test 4 ATP (ng/ml) | test 5 ATP (ng/ml) |
|---|---|---|
| 8.4 ppm | 0.7 | |
| 12.6 ppm | 0.56 | |
| 0 ppm | 0.61 | 0.61 |

The results presented in Table 3 show that after a contact time of 20 minutes, the biocide produced according to the procedure of Shim et al. (sodium hypochlorite stabilized with sulfamic acid added to water to be treated, then NaBr added thereafter to the water to be treated) is less effective in controlling microbial activity than the biocide produced in accordance with an embodiment of the present invention from sodium sulfamate, sodium bromide and sodium hypochlorite. This result is in accordance with the data presented by Shim, who states that antimicrobial efficacy of his product occurs only 24 hours or more after administration to the water to be treated.

Example 4

Total Aerobic Counts

General procedure for conducting viable count tests in this and other examples, unless noted otherwise: 10-fold serial dilutions of each of the following aqueous system test samples in sterile saline containing sodium thiosulfate were prepared 30 minutes after the biocide was added to the aqueous systems; the resulting serially ten-fold diluted solutions were mixed in the appropriate agar; colonies in the agar were counted after 48 hours incubation at 30° C., and are presented as cfu/ml.

Test 5 is the same test 5 conducted in Examples 2 and 3 above.

Test 6: A biocide was prepared by diluting a solution of sodium sulfamate (prepared from 14.62 g sodium sulfamate in 100 ml DI water containing 7.2 g NaOH, 5850 ppm) in DI water to produce a dilution equimolar to 4200 ppm chlorine, diluting sodium hypochlorite in DI water (to a concentration of 4200 ppm, 0.42% w/v), mixing the two dilutions and immediately adding an appropriate volume of the mixture to the aqueous system to be treated, as described above.

Samples for viable counts of aerobic MOs were taken after a contact time of 30 minutes. Results of Tests 5 and 6 are presented in Tables 4 and 4A.

TABLE 4

| treatment dosage, $Cl_2$ | Test 6 Aerobic cfu/ml | test 5 aerobic cfu/ml |
|---|---|---|
| 2.1 ppm | $1.30 \times 10^5$ | $5.86 \times 10^4$ |
| 0 ppm | $1.30 \times 10^5$ | $1.30 \times 10^5$ | cfu = colony forming units

TABLE 4A

| treatment dosage, $Cl_2$ | Test 6 aerobic cfu/ml (% kill) | test 5 Aerobic cfu/ml (% kill) |
|---|---|---|
| 2.1 ppm | 0% | 55% |

The results in Tables 4 and 4A demonstrate that producing a biocide by first producing a dilute mixture of bromide and sulfamate, then mixing this mixture with dilute hypochlorite and injecting the product into the liquid to be treated, while ensuring that there is no excess oxidant (hypochlorite) during the production of the biocide, yields a more efficacious biocide than does mixing a dilute sulfamate with dilute hypochlorite and injecting the product into the liquid to be treated.

Example 5

Viable Counts in Media Containing High Sugars

Test 7: A biocide was prepared by dissolving guanidinium sulfate in DI water (0.647 g guanidinium sulfate (MW 216.22) in 100 ml DI water), diluting sodium hypochlorite in DI water (to a concentration of 4200 ppm, 0.42% w/v expressed as $Cl_3$), mixing the two dilutions and immediately adding an appropriate volume of the mixture to the aqueous system to be treated, as described above.

Test 8: A biocide was prepared by mixing guanidinium sulfate (0.647 g) with NaBr (0.62 g, NaBr equimolar to sodium hypochlorite) in 100 ml DI water, diluting sodium hypochlorite in DI water (to a concentration of 4200 ppm, 0.42% w/v expressed as $Cl_2$), mixing the two dilutions and immediately adding an appropriate volume of the mixture to the aqueous system to be treated. The results are shown in Table 5, which shows the number of sugar-consuming colony forming units (cfu), and Table 5A, which present the same data as % survival relative to the non-biocide treated control.

TABLE 5

| treatment | Test 7 Sugar cfu/ml | test 8 sugar cfu/ml |
|---|---|---|
| 4.2 ppm, DI only | 0 | 0 |
| 2.1 ppm | $9.20 \times 10^2$ | $3.30 \times 10^2$ |
| 4.2 ppm | $9.80 \times 10^2$ | $4.00 \times 10$ |
| 6.3 ppm | $8.00 \times 10$ | $5.00 \times 10$ |
| 0 ppm | $1.06 \times 10^4$ | $1.06 \times 10^4$ |

TABLE 5A

| treatment | Test 7 sugar cfu/ml % survival | test 8 sugar cfu/ml % survival |
|---|---|---|
| 2.1 ppm | 8.68 | 3.11 |
| 4.2 ppm | 9.25 | 0.38 |
| 6.3 ppm | 0.75 | 0.42 |
| 0 ppm | 100.00 | 100.00 |

The results in Tables 5 and 5A demonstrate that under the conditions described, biocide produced by mixing guanidinium sulfate with dilute hypochlorite is less efficacious than biocide produced by first mixing guanidium sulfate and sodium bromide, and then mixing this mixture with dilute hypochlorite.

Example 6

Efficiency of Production of the Biocide

Residual total chlorine was measured in all of the control tests (biocide in DI water) of Tests 1-6 described above. The results are presented in Table 6.

TABLE 6

|  | % Cl$_2$ - 10 min | % Cl$_2$ - 20 Hours |
|---|---|---|
| test 1 (Shim et al.) | 59.5 | 54.8 |
| test 2 (Shim et al.) | 40.5 | 26.2 |
| test 3 (Shim et al.) | 48.8 | 38.1 |
| test 4 (Shim et al.) | 48.8 | 54.9 |
| test 5 | 119 | 107.1 |
| test 6 | 88.1 | 78.6 |

The results in Table 6 show that the "stabilized hypochlorite" and biocides produced in accordance with Shim et al. have a low initial residue compared to biocides formed in accordance with embodiments of the present invention. This demonstrates degradation of the biocide of Shim et al. during its production. In several instances the biocides produced by the method of Shim et al. also degrade faster during the first 20 hours after addition to the water to be treated.

Series 2

Reaction media were similar to the media described in Series 1.

Example 7

Comparison of Treatment of Aerobic and Anaerobic Bacteria Using Ammonium Carbamate and Ammonium Carbonate Biocides were prepared from sodium hypochlorite and either ammonium carbamate or ammonium carbonate in the presence and absence of sodium bromide, as described hereinbelow, and immediately added to the samples to be treated. The test containers were inoculated with MOs 48 hours prior to addition of biocide.

Ammonium carbonate solution was prepared in DI water (11.71 g ammonium carbonate in 100 ml DI water) and further diluted in DI water to a final concentration of 4680 ppm. Sodium hypochlorite was diluted in DI water (to a concentration of 4200 ppm, 0.42% w/v expressed as total chlorine). As described above, the dilutions were mixed to provide equimolar amounts of hypochlorite and ammonium carbonate to form a biocide (2100 ppm as total chlorine), appropriate volumes of which were immediately added to the test containers.

In an analogous manner, ammonium carbamate was prepared in DI water (11.71 g ammonium carbamate in 100 ml DI water) and further diluted in DI water to a concentration of 4680 ppm, and mixed with a dilute solution of sodium hypochlorite (4200 ppm, 0.46% w/v expressed as total chlorine), and appropriate volumes of the resulting biocide (2100 ppm as total chlorine) were immediately added to the test containers.

ATP was measured 25 minutes and 120 minutes after feeding the biocide. Residual total chlorine was measured 5 minutes after feeding the biocide, and samples for viable counts were taken after 30 minutes contact time.

The tests were repeated, this time with mixing of sodium bromide (6200 ppm) with the ammonium carbonate or ammonium carbamate prior to mixing with the sodium hypochlorite.

Counts of ATP, total aerobic bacteria, growth on a high sugar growth medium, and killing of anaerobic bacteria were measured. The results are presented in Tables 7A-7E.

TABLE 7A

Comparison of ATP levels (ng/ml) measured after 25 min

| treatment | Ammonium carbonate | ammonium carbonate + NaBr | ammonium carbamate | Ammonium carbamate + NaBr |
|---|---|---|---|---|
| 1.4 ppm | 25.87 |  | 30.7 |  |
| 2.8 ppm | 20 | 17.2 | 19.2 | 13.5 |
| 5.6 ppm | 8.8 | 21.2 | 10.13 | 26.7 |
| 8.4 ppm | 16 |  | 6.7 |  |
| 14 ppm |  | 2.6 | 2.3 | 3.33 |
| 28 ppm |  | 1.59 |  | 1.16 |
| Blank | 15.6 |  |  | 40 |

TABLE 7B comparison of ATP levels (ng/ml) measured after 120 min - regrowth potential

| Treatment | Ammonium carbonate | ammonium carbonate + NaBr | ammonium carbamate | Ammonium carbamate + NaBr |
|---|---|---|---|---|
| 1.4 ppm | 89.3 |  | 66.7 |  |
| 2.8 ppm | 101.3 | 109.3 | 81.33 | 117.33 |
| 5.6 ppm | 41.3 | 29.3 | 23.3 | 23.33 |
| 8.4 ppm | 8.9 |  | 2.5 |  |
| 14 ppm |  | 1.43 | 0.77 | 1.05 |
| 28 ppm |  | 0.47 |  | 0.22 |
| Blank | 94.7 |  |  | 110.7 |

TABLE 7C comparison of total aerobic bacteria count, cfu/ml after 30 min contact time

| Treatment | ammonium carbonate | ammonium carbonate + NaBr | ammonium carbamate | ammonium carbamate + NaBr |
|---|---|---|---|---|
| 1.4 ppm | $3.00 \times 10^8$ |  | $5.00 \times 10^7$ |  |
| 2.8 ppm | $5.00 \times 10^7$ | $2.70 \times 10^7$ | $1.10 \times 10^7$ | $2.40 \times 10^7$ |
| 5.6 ppm | $5.00 \times 10^6$ | $9.44 \times 10^6$ | $7.60 \times 10^6$ | $3.20 \times 10^6$ |
| 8.4 ppm | $4.00 \times 10^6$ |  | $6.60 \times 10^4$ |  |
| 14 ppm |  | $3.20 \times 10^5$ | $3.60 \times 10^4$ | $2.80 \times 10^5$ |
| 28 ppm |  | $4.40 \times 10^4$ |  | $4.16 \times 10^4$ |
| Blank | $4.80 \times 10^7$ | $4.80 \times 10^7$ | $4.60 \times 10^7$ | $4.60 \times 10^7$ |

TABLE 7D comparison of growth on a high sugar growth medium (cfu/ml), after 30 min contact time

| Treatment | ammonium carbonate | ammonium carbonate + NaBr | ammonium carbamate | ammonium carbamate + NaBr |
|---|---|---|---|---|
| 1.4 ppm | $3.00 \times 10^7$ |  | $3.00 \times 10^7$ |  |
| 2.8 ppm | $3.00 \times 10^7$ | $1.22 \times 10^5$ | $1.10 \times 10^5$ | $4.00 \times 10^3$ |
| 5.6 ppm | $3.00 \times 10^7$ | $1.80 \times 10^4$ | $1.00 \times 10^2$ | $1.00 \times 10^3$ |
| 8.4 ppm | $3.00 \times 10^4$ |  | $1.00 \times 10^1$ |  |
| 14 ppm |  | $2.00 \times 10^2$ | $1.00 \times 10^1$ | $1.00 \times 10^1$ |
| 28 ppm |  | $2.00 \times 10^2$ |  | $2.00 \times 10^1$ |
| Blank | $5.00 \times 10^7$ |  |  | $3.00 \times 10^8$ |

TABLE 7E total anaerobic counts (cfu/ml), after 30 min contact time

| Treatment | ammonium carbonate | ammonium carbonate + NaBr | ammonium carbamate | ammonium carbamate + NaBr |
|---|---|---|---|---|
| 1.4 ppm | $3.00 \times 10^7$ | | | |
| 2.8 ppm | $2.00 \times 10^6$ | $1.00 \times 10^4$ | $3.00 \times 10^7$ | $1.00 \times 10^3$ |
| 5.6 ppm | $5.00 \times 10^6$ | $2.10 \times 10^4$ | $3.40 \times 10^4$ | $1.00 \times 10^3$ |
| 8.4 ppm | $2.00 \times 10^3$ | | $3.00 \times 10^3$ | |
| 14 ppm | | $1.00 \times 10^2$ | $1.00 \times 10^1$ | $2.00 \times 10^2$ |
| 28 ppm | | $1.00 \times 10^2$ | $1.00 \times 10^1$ | $1.00 \times 10^2$ |
| Blank | $3.00 \times 10^7$ | | | $3.00 \times 10^7$ |

Series 3

Example 8

Comparison of Biocidal Properties of Biocides Prepared from Ammonium Sulfamate Ammonium Sulfate, Sulfamic Acid and Ammonium Carbamate Reaction medium: 4 liters DI water containing 200 ml cooked starch, 5.29 g $NaHCO_3$, and 0.52 g CaO. The pH was adjusted with HCl to 8.23.

As described in earlier examples, biocides were prepared as follows:

Test 9: Sulfamic acid solution (14.62 g sulfamic acid in 100 ml DI water) was diluted (4 ml of solution in 100 ml DI water) and $NH_3$ (0.5 ml, 25% w/v in water) was added. Diluted NaOCl (4 ml of a solution containing 14% w/v NaOCl as $Cl_2$ were diluted in 100 ml DI water) was mixed with the diluted sulfamic acid.

Test 10: Ammonium sulfate solution (19.8 g/100 ml DI water) was diluted (2 ml of solution/100 ml DI water). NaOCl solution (14% w/v as $Cl_2$ in water) was diluted in DI water (4 ml of solution/100 ml), and mixed with the diluted ammonium sulfate solution.

Test 11: Sulfamic acid solution (14.62 g/100 ml DI water) was diluted (4 ml solution/100 ml DI water) and mixed with diluted NaOCl (4 ml of 14% w/v as $Cl_2$ NaOCl solution/100 ml DI water).

Test 12: Ammonium carbamate solution (11.55 g/100 ml DI water) was diluted (4 ml solution/100 ml DI water) and mixed with diluted NaOCl (4 ml of 14% w/v as $Cl_2$ NaOCl solution/100 ml DI water).

In tests 9-12, an appropriate volume of the resulting biocide was immediately added to water containing MOs from pink slime, as described above, and the total residual chlorine in the treated water/medium was measured after 5 minutes and 12 hours. Results are presented in Tables 8A and 8B.

TABLE 8A

Total residual chlorine after 5 minutes (ppm):

| feed as $Cl_2$ (ppm) | 5 min $H_2NSO_3NH_4$ | 5 min $(NH_4)_2SO_4$ | 5 min $H_2NSO_3H$ | 5 min $H_2NCO_2NH_4$ |
|---|---|---|---|---|
| 1.4 (control - DI water only) | 1.4 | 1.6 | 0.9 | 1.2 |
| 1.4 | 0 | 0 | 0.3 | 0 |
| 2.8 | 1.3 | 0.9 | 0.7 | 0.2 |
| 7 | 4.9 | 5 | 4 | 1.3 |
| 14 | 10.7 | 8.1 | 10.7 | 10.2 |

TABLE 8B

Total residual chlorine after 12 hours (ppm):

| feed as $Cl_2$ (ppm) | 12 hours $H_2NSO_3NH_4$ | 12 hours $(NH_4)_2SO_4$ | 12 hours $H_2NSO_3H$ | 12 hours $H_2NCO_2NH_4$ |
|---|---|---|---|---|
| 1.4 (control - DI water only) | 1.1 | 1.1 | 0.9 | 1.2 |
| 1.4 | 0 | 0 | 0.3 | 0 |
| 2.8 | 0.1 | 0 | 0.3 | 0.2 |
| 7 | 1.1 | 1.2 | 2.9 | 1.3 |
| 14 | 4.1 | 3.8 | 9.2 | 3.9 |

The results in Tables 8A and 8B show that the biocides derived from sulfamic acid and from ammonium sulfamate were the most stable biocides after 5 minutes. The biocide derived from sulfamic acid remained stable and exhibited high residual total chlorine after 12 hours.

ATP values for MOs growing on growth medium treated with the biocides produced in Tests 9-12 were obtained 30 minutes and 12 hours after addition of biocide to the growth medium. The results are shown in Tables 8C and 8D.

TABLE 8C

ATP measured 20 minutes after feeding the biocide (rlu)

| feed as $Cl_2$ (ppm) | ATP-20 min $H_2NSO_3NH_4$ | ATP-20 min $(NH_4)_2SO_4$ | ATP-20 min $H_2NSO_3H$ | ATP-20 min $H_2NCO_2NH_4$ |
|---|---|---|---|---|
| 1.4 | 25500 | 24000 | 31500 | 39000 |
| 2.8 | 19500 | 28500 | 26000 | 16500 |
| 7 | 9950 | 16000 | 26000 | 14000 |
| 14 | 5200 | 2850 | 12000 | 4500 |
| Blank | 24500 | 20500 | 37000 | 29000 |

TABLE 8D

ATP measured 12 hours after feeding the biocide (rlu)

| feed as $Cl_2$ (ppm) | ATP-12 h $H_2NSO_3NH_4$ | ATP-12 h $(NH_4)_2SO_4$ | ATP-12 h $H_2NSO_3H$ | ATP-12 h $H_2NCO_2NH_4$ |
|---|---|---|---|---|
| 1.4 | 90000 | 94500 | 83000 | 87500 |
| 2.8 | 8550 | 6000 | 76000 | 3950 |
| 7 | 435 | 460 | 42000 | 560 |
| 14 | 380 | 390 | 14500 | 300 |
| blank | 87500 | 90000 | 95500 | 95500 |

Conclusions: at a feed level of 1.4 ppm, no control was achieved, and the MOs continued to grow. A feed level of 2.8 ppm as total chlorine was ineffective for biocide formed from sulfamic acid, despite the higher residual left in the process water. At 2.8 ppm, better control was achieved with ammonium sulfate compared to sodium sulfamate, and still better control with ammonium carbamate after 30 minutes as well as after 12 hours.

The test samples of Tests 9-12 were checked for viable counts of aerobic, anaerobic and high-sugar MOs (cfu/ml) after a contact time of 30 minutes. The results are presented in Tables 8E-8G.

TABLE 8E

Effect of biocides on growth of aerobic MOs, contact time 30 minutes

| feed as $Cl_2$ (ppm) | aerobic MOs (cfu/ml), 30 minutes | | | |
|---|---|---|---|---|
| | $H_2NSO_3NH_4$ | $(NH_4)_2SO_4$ | $H_2NSO_3H$ | $H_2NCO_2NH_4$ |
| 1.4 | $1.29 \times 10^6$ | $1.40 \times 10^6$ | $1.08 \times 10^6$ | $9.70 \times 10^5$ |
| 2.8 | $6.16 \times 10^5$ | $6.40 \times 10^5$ | $5.40 \times 10^5$ | $8.96 \times 10^5$ |
| 7 | $4.00 \times 10^5$ | $3.60 \times 10^5$ | $8.08 \times 10^5$ | $5.84 \times 10^5$ |
| 14 | $2.40 \times 10^5$ | $1.80 \times 10^5$ | $7.36 \times 10^5$ | $7.50 \times 10^4$ |
| blank | $1.20 \times 10^6$ | $1.44 \times 10^6$ | $1.10 \times 10^6$ | $1.34 \times 10^6$ |

TABLE 8F

Effect of biocides on growth of anaerobic MOs, contact time 30 minutes

| feed as $Cl_2$ (ppm) | Anaerobic MOs (cfu/ml), 30 minutes | | | |
|---|---|---|---|---|
| | $H_2NSO_3NH_4$ | $(NH_4)_2SO_4$ | $H_2NSO_3H$ | $H_2NCO_2NH_4$ |
| 1.4 | $1.50 \times 10^3$ | $1.00 \times 10^1$ | $2.50 \times 10^3$ | $1.00 \times 10^1$ |
| 2.8 | $1.00 \times 10^1$ | $1.00 \times 10^1$ | $1.00 \times 10^1$ | $1.00 \times 10^1$ |
| 7 | $1.00 \times 10^1$ | $1.00 \times 10^1$ | $2.00 \times 10^2$ | $1.00 \times 10^1$ |
| 14 | $1.00 \times 10^1$ | $1.00 \times 10^1$ | $3.00 \times 10^2$ | $1.00 \times 10^1$ |
| blank | $1.00 \times 10^3$ | $1.00 \times 10^3$ | $1.00 \times 10^3$ | $1.00 \times 10^3$ |

TABLE 8G

Effect of biocides on growth of high-sugar MOs, contact time 30 minutes

| feed as $Cl_2$ (ppm) | High sugar MOs (cfu/ml), 30 min | | | |
|---|---|---|---|---|
| | $H_2NSO_3NH_4$ | $(NH_4)_2SO_4$ | $H_2NSO_3H$ | $H_2NCO_2NH_4$ |
| 1.4 | $6.24 \times 10^4$ | $1.03 \times 10^5$ | $6.40 \times 10^4$ | $1.79 \times 10^5$ |
| 2.8 | $5.00 \times 10^2$ | $4.00 \times 10^2$ | $3.32 \times 10^4$ | $2.00 \times 10^2$ |
| 7 | $1.00 \times 10^1$ | $1.00 \times 10^1$ | $8.72 \times 10^4$ | $1.00 \times 10^1$ |
| 14 | $1.00 \times 10^1$ | $1.00 \times 10^1$ | $7.30 \times 10^3$ | $1.00 \times 10^1$ |
| Blank | $1.20 \times 10^5$ | $1.10 \times 10^5$ | $7.00 \times 10^4$ | $1.10 \times 10^5$ |

The results shown in Tables 8E-8G clearly show differences in viable counts after a contact time of 30 minutes. The biocide produced from ammonium carbamate was superior to the other biocides tested in controlling aerobic MOs.

Series 4

Example 9

Comparison of Biocidal Properties of Biocides Prepared from Different Nitrogen-Containing Compounds or Salts Test medium A: 500 ml of contaminated clay suspension and 200 ml of cooked starch was mixed with 5 liters of tap water and inoculated with biofilm removed from a paper mill surface area.

Test medium B: 0.46 g sodium sulfide was added to 2 liters of the clay slurry of Test medium A.

Due to the high turbidity of the samples, reliable measurement of residual total chlorine was not possible. Qualitative measure of total chlorine confirmed that most of the biocide was consumed by this test medium.

Samples for viable counts were removed after a contact time of 1 hour.

As described above, biocides were prepared by mixing dilutions of the following with diluted sodium hypochlorite:

| Test No. | species | molar ratio to NaOCl |
|---|---|---|
| 13 | mixture of glycine and ammonium hydroxide | 1:1 |
| 14 | ammonium sulfamate | 1:1 |
| 15 | methyl carbamate | 1:1 |
| 16 | N,N-dimethyl ammonium N,N-dimethyl carbamate | 1:1 |
| 17 | ammonium carbamate + HCl (HCl was added to ammonium carbamate prior to mixing with NaOCl, to ensure biocide production at a pH of 9.2) | 1:1 |
| 18 | ammonium sulfate | 2:1 |
| 19 | ammonium sulfate | 2:1 |
| 20 | ammonium carbamate + HCl (HCl was added to ammonium carbamate prior to mixing with NaOCl, to ensure biocide production at a pH of 8.7) | 1:1 |
| 21 | control | — |

The biocides formed were immediately added in appropriate volumes to the test samples and the concentrations of aerobic and anaerobic MOs measured. pH was measured at the time of application of the biocide and two days later. The concentrations at which biocides were applied and the results of biocide application to test medium A are presented in Table 9A; the concentrations at which biocides were applied and the results of biocide application to test medium B are presented in Table 9B.

TABLE 9A

| TEST | Feed level (as $Cl_2$, ppm) | aerobic | anaerobic | pH day 1 | pH day 3 |
|---|---|---|---|---|---|
| 13CA | 12 | $1.10 \times 10^5$ | $1.24 \times 10^4$ | 7.5 | 7.3 |
| 13CB | 20 | $1.10 \times 10^5$ | $1.04 \times 10^4$ | 7.71 | 7.58 |
| 14CA | 12 | $8.10 \times 10^4$ | $2.00 \times 10^3$ | 7.42 | 7.58 |
| 14CB | 20 | $3.30 \times 10^4$ | $8.20 \times 10^2$ | 7.43 | 7.38 |
| 15CA | 12 | $8.90 \times 10^4$ | $8.00 \times 10^3$ | 7.38 | 7.49 |
| 15CB | 20 | $8.20 \times 10^4$ | $3.64 \times 10^3$ | 7.56 | 7.56 |
| 16CA | 12 | $1.50 \times 10^5$ | $2.00 \times 10^1$ | 7.65 | 7.4 |
| 16CB | 20 | $8.60 \times 10^4$ | 1.00 | 7.75 | 7.37 |
| 17CA | 12 | $8.90 \times 10^4$ | $1.00 \times 10$ | 7.66 | 7.61 |
| 17CB | 20 | $1.70 \times 10^4$ | 1.00 | 8.04 | 7.44 |
| 18CA | 12 | $9.00 \times 10^4$ | $6.80 \times 10^3$ | 7.41 | 7.23 |
| 18CB | 20 | $3.30 \times 10^4$ | $1.44 \times 10^3$ | 7.45 | 7.52 |
| 19CA | 12 | $1.90 \times 10^5$ | 1.00 | 7.45 | 7.32 |
| 19CB | 20 | $1.20 \times 10^5$ | $2.00 \times 10$ | 7.53 | 7.27 |
| 20CA | 12 | $1.90 \times 10^5$ | $2.00 \times 10$ | 7.52 | 7.29 |
| 20CB | 20 | $1.80 \times 10^5$ | $3.60 \times 10^3$ | 7.78 | 7.4 |
| 21C | 0 | $9.90 \times 10^5$ | $1.00 \times 10^4$ | 7.44 | 7.26 |

TABLE 9B

| TEST | Feed level (as $Cl_2$, ppm) | aerobic | anaerobic | pH day 1 | pH day 3 |
|---|---|---|---|---|---|
| 13SA | 20 | $2.20 \times 10^5$ | $3.00 \times 10^4$ | 8.18 | 7.43 |
| 13SB | 24 | $1.60 \times 10^5$ | $3.00 \times 10^4$ | 8.29 | 7.35 |
| 14SA | 20 | $4.50 \times 10^4$ | $1.70 \times 10^2$ | 8.31 | 7.66 |
| 14SB | 24 | $2.50 \times 10^4$ | $2.60 \times 10^3$ | 8.48 | 7.46 |
| 15SA | 32 | $9.50 \times 10^4$ | $3.00 \times 10^4$ | 8.49 | 7.63 |
| 15SB | 36 | $7.60 \times 10^4$ | $3.00 \times 10^4$ | 8.64 | 8.47 |
| 16SA | 32 | $1.60 \times 10^5$ | 1.00 | 8.29 | 7.6 |
| 16SB | 36 | $1.50 \times 10^5$ | 1.00 | 8.49 | 7.57 |
| 17SA | 32 | $8.70 \times 10^3$ | 1.00 | 8.74 | 8.68 |
| 17SB | 36 | $6.60 \times 10^3$ | 1.00 | 8.85 | 8.82 |
| 18SA | 20 | $2.40 \times 10^5$ | $3.00 \times 10^4$ | 8.01 | 7.35 |
| 18SB | 24 | $1.40 \times 10^5$ | $3.00 \times 10^4$ | 8.24 | 7.58 |
| 19SA | 32 | $3.00 \times 10^4$ | 1.00 | 8.35 | 8.36 |
| 19SB | 36 | $1.70 \times 10^3$ | 1.00 | 8.41 | 8.48 |
| 20SA | 32 | $1.60 \times 10^4$ | 1.00 | 8.63 | 8.6 |
| 20SB | 36 | $8.10 \times 10^3$ | 1.00 | 8.67 | 8.64 |
| 21S (control) | 0 | $9.20 \times 10^5$ | $3.00 \times 10^4$ | 7.8 | 7.37 |

The results presented in Tables 9A and 9B show that in spite of the high demand for oxidizer in the media, and the trace residual chlorine measured using the given biocide feed levels, biocides produced from ammonium carbamate and ammonium sulfamate controlled the growth of MOs in the heavily infested samples.

Series 5

Two test media were used:

CLAY: 200 ml of clay suspension was added to 2 liters of tap water at pH 7.04. Test medium was inoculated with MOs from a paper mill.

CLAY+ACID: 200 ml of clay suspension was added to 2 liters of tap water and the pH was reduced to 6.12 by addition of HCl. Starch (100 ml cooked starch) was added. The test medium was not inoculated with external MOs.

All test samples were fed with 20 ppm biocide as total chlorine.

Example 10

As described above, biocides were prepared by mixing dilutions of the following and dilute sodium hypochlorite:

| Test No. | species | molar ratio to NaOCl |
|---|---|---|
| 22 | Control - no biocide | |
| 23 | ammonium carbamate | 1:1 |
| 24 | ammonium sulfate | 1:1 |
| 25 | ammonium carbonate | 1:1 |
| 26 | ammonium carbamate + HCl (HCl added to reduce pH to 9.22) | 1:1 |

Appropriate amounts of the biocides formed were immediately added to the test samples and aerobic and anaerobic viable counts were measured 60 minutes after application. pH was measured at the time of application of the biocide and three days later. The concentrations at which biocides were applied and the results of biocide application are presented in Table 10.

TABLE 10

| TEST | conditions | Conc. (as $Cl_2$, ppm) | aerobic | anaerobic | pH day 1 | pH day 3 |
|---|---|---|---|---|---|---|
| 22A | clay + acid | 0 | $5.00 \times 10^4$ | $1.02 \times 10^4$ | 6.64 | Data not available |
| 22C | clay | 0 | $1.50 \times 10^7$ | $6.00 \times 10^3$ | 7.4 | 7.22 |
| 23CB | clay | 20 | $3.00 \times 10^6$ | $2.12 \times 10^3$ | 7.55 | 7.82 |
| 23AB | clay + acid | 20 | $3.08 \times 10^4$ | $5.28 \times 10^3$ | 6.93 | 7.06 |
| 24CB | clay | 20 | $8.00 \times 10^5$ | $2.00 \times 10^3$ | 7.34 | 7.16 |
| 24AB | clay + acid | 20 | $2.80 \times 10^4$ | $8.56 \times 10^3$ | 6.6 | 7.05 |
| 25CB | clay | 20 | $3.00 \times 10^6$ | $1.84 \times 10^3$ | 7.41 | 7.24 |
| 25AB | clay + acid | 20 | $1.09 \times 10^4$ | $4.96 \times 10^3$ | 6.76 | 7.03 |
| 26CB | clay | 20 | $3.00 \times 10^7$ | $2.52 \times 10^3$ | 7.72 | 7.34 |
| 26AB | clay + acid | 20 | $5.40 \times 10^4$ | $1.60 \times 10^4$ | 6.88 | 6.69 |

Series 6

Reaction media: 0.34 g of $Na_2S$ were added to 2 liters of tap water containing 200 ml cooked starch slurry. Initial ORP: −263 mv. As the starch was naturally inoculated, this test medium was not inoculated with an external culture of microorganisms.

Example 11

By analogy to Example 9, biocides were prepared using the following species and sodium hypochlorite in the following ratios:

| Test No. | species | molar ratio to NaOCl |
|---|---|---|
| 27 | ammonium carbonate | 1:1 |
| 28 | ammonium cyanurate | 1:1 |
| 29 | ammonium sulfamate | 1:1 |
| 30 | ammonium carbamate | 1:1 |
| 31 | 1:1 mixture of ammonium carbamate and carbamic acid (HCl added to lower pH to 9.2) | 1:1 |
| 32 | ammonium bromide | 1:1 |
| 33 | ammonium carbamate | 2:1 |
| 34 | control | — |

Results, including total chlorine, are shown in Table 11:

TABLE 11

| TEST | Feed level (as $Cl_2$, ppm) | total chlorine (ppm) | aerobic | anaerobic | pH day 1 | pH day 3 | pH day 4 |
|---|---|---|---|---|---|---|---|
| 27A | 47 | 2.5 | $8.80 \times 10^5$ | 1.00 | 8.94 | 8.85 | 7.67 |
| 28A | 47 | 0.9 | $3.00 \times 10^6$ | 1.00 | 8.88 | 7.98 | 7.5 |
| 29A | 47 | 1.2 | $3.00 \times 10^6$ | 1.00 | 8.83 | 7.99 | 7.43 |
| 30A | 47 | 6 | $5.12 \times 10^5$ | 1.00 | 9.12 | 9.1 | 8.19 |
| 31A | 47 | 1.5 | $2.00 \times 10^6$ | 1.00 | 8.94 | 8.3 | 7.55 |
| 32A | 47 | 2.4 | $1.00 \times 10^6$ | 1.00 | 8.88 | 8.79 | 7.58 |
| 33A | 47 | 4.9 | $1.50 \times 10^3$ | 1.00 | 9.1 | 9.07 | 8.71 |
| 34A | 0 | 0 | $8.00 \times 10^6$ | 1.00 | 8.51 | 7.72 | 7.45 |

This experiment presents a special case of extremely high demand for an oxidizer exerted by the presence of a strong reducing agent ($Na_2S$) and starch and degradation byproducts thereof which are produced by the heavy microbial population that infests starch. Extreme conditions such as these may frequently be found in industrial and agricultural environments, such as soil, recycling processes, activated sludge and waste and the like.

Example 12

Biocides were prepared by analogy to Example 9, but the biocides were applied to a clay slurry, as described in Example 10, and additional biocides were prepared in the same way but wherein NaBr (equimolar to hypochlorite and nitrogen-containing compound or salt thereof) was added to the nitrogen-containing compound or salt thereof prior to dilution and mixing with the hypochlorite dilution. Results are shown in Tables 12A and 12B.

TABLE 12A

| TEST | Conc. (as $Cl_2$, ppm) | Aerobic | anaerobic |
|---|---|---|---|
| 13CA | 12 | $1.10 \times 10^5$ | $1.24 \times 10^4$ |
| 13CB | 20 | $1.10 \times 10^5$ | $1.04 \times 10^4$ |
| 14CA | 12 | $8.10 \times 10^4$ | $2.00 \times 10^3$ |
| 14CB | 20 | $3.30 \times 10^4$ | $8.20 \times 10^2$ |
| 15CA | 12 | $8.90 \times 10^4$ | $8.00 \times 10^3$ |
| 15CB | 20 | $8.20 \times 10^4$ | $3.64 \times 10^3$ |
| 16CA | 12 | $1.50 \times 10^5$ | $2.00 \times 10$ |
| 16CB | 20 | $8.60 \times 10^4$ | 1.00 |
| 17CA | 12 | $8.90 \times 10^4$ | $1.00 \times 10$ |
| 17CB | 20 | $1.70 \times 10^4$ | 1.00 |
| 18CA | 12 | $9.00 \times 10^4$ | $6.80 \times 10^3$ |
| 18CB | 20 | $3.30 \times 10^4$ | $1.44 \times 10^3$ |
| 19CA | 12 | $1.90 \times 10^5$ | 1.00 |
| 19CB | 20 | $1.20 \times 10^5$ | $2.00 \times 10^1$ |
| 20CA | 12 | $1.90 \times 10^5$ | $2.00 \times 10^1$ |
| 20CB | 20 | $1.80 \times 10^5$ | $3.60 \times 10^3$ |
| 21C | 0 | $9.90 \times 10^5$ | |

CA, CB = no NaBr added during biocide production

TABLE 12B

| TEST | Conc. (as $Cl_2$, ppm) | Aerobic | anaerobic |
|---|---|---|---|
| 13CC | 20 | $9.30 \times 10^4$ | $8.96 \times 10^3$ |
| 13CD | 28 | $9.60 \times 10^4$ | $1.04 \times 10^3$ |
| 14CC | 20 | $1.10 \times 10^5$ | $1.46 \times 10^3$ |
| 14CD | 28 | $9.00 \times 10^4$ | $1.52 \times 10^2$ |
| 15CC | 20 | $6.80 \times 10^4$ | $8.00 \times 10^3$ |
| 15CD | 28 | $4.80 \times 10^5$ | $2.72 \times 10^3$ |
| 16CC | 20 | $6.60 \times 10^4$ | 1.00 |
| 16CD | 28 | $3.80 \times 10^4$ | 1.00 |
| 17CC | 20 | $5.00 \times 10^4$ | $2.00 \times 10$ |
| 17CD | 28 | $1.50 \times 10^4$ | 1.00 |
| 18CC | 12 | $3.90 \times 10^4$ | $2.00 \times 10^3$ |
| 18CD | 20 | $1.30 \times 10^4$ | $6.40 \times 10^2$ |
| 19CC | 20 | $1.90 \times 10^5$ | $2.00 \times 10^1$ |
| 19CD | 28 | $5.90 \times 10^4$ | $4.00 \times 10^1$ |
| 20CC | 20 | $8.00 \times 10^4$ | $1.00 \times 10^0$ |
| 20CD | 28 | $1.20 \times 10^4$ | $1.00 \times 10^1$ |
| 21C | 0 | $9.90 \times 10^5$ | |

CC, CD = NaBr added during biocide production

Series 7

Reduction of $Na_2S$

A series of containers each containing 100 ml DI water in which ~5 mg of sodium sulfide was dissolved were prepared. To each container an appropriate amount of an oxidizer or a control solution was added as follows:

a. 0.08 g $NaNO_2$
b. ammonium carbamate (110 mg)
c. Monochloroamine (MCA) formed from ammonium sulfate and NaOCl (1:1 molar ratio, each component pre-diluted before mixing, 15 ppm as total chlorine).
d. MCA formed from ammonium sulfate and NaOCl (1:1 molar ratio, each component pre-diluted before mixing, 15 ppm as total chlorine)+ammonium carbamate (110 mg).
e. Reaction product of ammonium carbamate and sodium hypochlorite (15 ppm as total chlorine) (1:1 molar ratio)+100 ppm ammonium carbamate
f. Reaction product of ammonium carbamate and sodium hypochlorite (15 ppm as total chlorine), molar ratio 2:1
g. Reaction product of ammonium carbamate and sodium hypochlorite (15 ppm as chlorine), molar ratio 1:1
h. Reaction product of ammonium bromide and sodium hypochlorite (15 ppm as chlorine), molar ratio 1:1, +ammonium carbamate (100 mg).
i. Reaction product of ammonium bromide and ammonium carbamate with sodium hypochlorite (15 ppm as chlorine), molar ratio 1:1:1

Samples were analyzed for total sulfur and for sulfate several days after addition of oxidizer. The results are presented in Table 13:

TABLE 13

| Test | % S remaining | % $SO_4$ formed |
|---|---|---|
| A | 100 | 0 |
| B | 19.6 | 45.63 |
| C | 3.92 | 37.1 |
| D | <2 | 24.7 |
| E | 2 | <16.9 |
| F | 3.9 | 16.9 |
| G | 1.96 | 13 |
| H | 17.6 | 50.8 |
| I | 15.7 | 24 |

The results in Table 13 demonstrate that ammonium carbamate can remove sulfides, and that upon reaction with NaOCl or with mixtures containing chloramines, ammonium carbamate retains high efficacy in removing sulfides from the treated samples.

Series 8

Reactions of Nitrogen-Containing Compounds

Reaction MEDIA:

SAND: 250 g sand was added to 2.5 l tap water containing 100 g contaminated starch.

ASA: 150 ml $CaCO_3$ slurry and 20 ml Bayer size ASA (alkenyl succinic anhydride). The slurry was inoculated with pieces of slime from a paper mill. 1 ml OBA (Optical brightening agent, a Triazine derivative) was added to each 100 ml of the test solution.

The following nitrogen-containing compounds or salts were tested:

Test 35=Dimethyl hydantoin (DMH)+$NH_4OH$
Test 36=ammonium carbamate
Test 37=ammonium sulfamate
Test 38=sulfamic acid
Test 39=glutamine
Test 40=ammonium chloride
Test 41=ammonium bromide
Test 42=blank Each nitrogen-containing compound or salt was mixed with diluted NaOCl, and the reaction product was added to the reaction container in the appropriate amount as soon as the biocide was prepared. Prior to addition to the reaction container, the biocide contained 4000 ppm as total chlorine.

The results of tests in SAND (sand+starch) are presented in Table 14:

TABLE 14

| N-cont. cmpd. | feed level (ppm) | total chlorine 10 min. (ppm) | aerobic (cfu) | anaerobic (cfu) | $Cl_2$ after 1 h (ppm) | pH after three weeks |
|---|---|---|---|---|---|---|
| 40 | 8 | 3 | $7.50 \times 10^4$ | $3.00 \times 10$ | 4.3 | 6.97 |
| 40 | 12 | 6 | $1.68 \times 10^4$ | $4.00 \times 10$ | 7.5 | 6.89 |
| 35 | 8 | 5.6 | $1.84 \times 10^4$ | $1.00 \times 10$ | 4.3 | 6.84 |
| 35 | 12 | 7.5 | $8.80 \times 10^2$ | $2.00 \times 10$ | 6.8 | 6.94 |
| 36 | 8 | 4.9 | $4.40 \times 10^3$ | $6.00 \times 10$ | 4.8 | 6.9 |
| 36 | 12 | 7.2 | $6.00 \times 10^2$ | $1.00 \times 10$ | 6.8 | 7.46 |
| 37 | 8 | 5.6 | $1.02 \times 10^3$ | $5.00 \times 10$ | 5.3 | 6.9 |
| 37 | 12 | 8.3 | $7.00 \times 10^2$ | $1.00 \times 10$ | 7.6 | 6.88 |
| 38 | 8 | 1.9 | $2.00 \times 10^5$ | $1.00 \times 10^4$ | 1.1 | 5.15 |
| 38 | 12 | 2.7 | $1.50 \times 10^5$ | $6.00 \times 10^3$ | 2 | 5.79 |
| 39 | 8 | 6.1 | $3.00 \times 10^6$ | $3.00 \times 10^4$ | 1.9 | 4.12 |
| 39 | 12 | 8.4 | $3.00 \times 10^6$ | $3.00 \times 10^4$ | 3.4 | 4.07 |
| 40 | 8 | 5 | $1.07 \times 10^3$ | $3.00 \times 10$ | 4 | 6.78 |
| 40 | 12 | 8.5 | $5.00 \times 10^2$ | $2.00 \times 10$ | 7.1 | 6.84 |
| 42 control | 0 | 0 | $1.15 \times 10^7$ | $5.92 \times 10^4$ | 0 | 4.25 |

The results of tests in ASA ($CaCO_3$+ASA) are presented in Table 15:

TABLE 15

| N-cont. cmpd. | feed level (ppm) | total chlorine 10 min. (ppm) | aerobic (cfu) | anaerobic (cfu) | $Cl_2$ after 1 h | pH after three weeks |
|---|---|---|---|---|---|---|
| 40 | 8 | 5.3 | $2.82 \times 10^5$ | 1.00 | 5.1 | 7.53 |
| 40 | 12 | 8 | $9.52 \times 10^4$ | $1.00 \times 10$ | 8.2 | 7.63 |
| 35 | 8 | 4.9 | $1.50 \times 10^5$ | 1.00 | 4.2 | 7.6 |
| 35 | 12 | 7.5 | $8.16 \times 10^4$ | $1.00 \times 10$ | 7.5 | 7.67 |
| 36 | 8 | 5.3 | $1.00 \times 10^5$ | $3.00 \times 10$ | 4.5 | 7.59 |
| 36 | 12 | 5.3 | $1.00 \times 10^5$ | $1.00 \times 10$ | 4.2 | 7.62 |
| 37 | 8 | 4.8 | $1.50 \times 10^5$ | $2.00 \times 10$ | 4.7 | 7.55 |
| 37 | 12 | 8.2 | $1.00 \times 10^5$ | $1.00 \times 10$ | 8 | 7.82 |
| 38 | 8 | 1.1 | $3.00 \times 10^6$ | $3.00 \times 10^3$ | 1.2 | 7.52 |
| 38 | 12 | 1.1 | $3.00 \times 10^5$ | $2.20 \times 10^3$ | 2.3 | 7.48 |
| 39 | 8 | 5.3 | $3.00 \times 10^5$ | $3.00 \times 10^4$ | 2.8 | 7.41 |

TABLE 15-continued

| N-cont. cmpd. | feed level (ppm) | total chlorine 10 min. (ppm) | aerobic (cfu) | anaerobic (cfu) | Cl$_2$ after 1 h | pH after three weeks |
|---|---|---|---|---|---|---|
| 39 | 12 | 7.6 | $3.00 \times 10^6$ | $3.00 \times 10^4$ | 3.9 | 7.39 |
| 40 | 8 | 3.9 | $1.50 \times 10^5$ | $2.00 \times 10$ | 4.5 | 8.24 |
| 40 | 12 | 5.9 | $3.20 \times 10^4$ | $1.00 \times 10$ | 7.9 | 8.16 |
| 42 control | 0 | 0 | $5.84 \times 10^6$ | $1.60 \times 10^4$ | 0 | 8.23 |

The results in Tables 14 and 15 show that biocides derived from compounds containing an amide moiety, an imide moiety, a sulfamide moiety, a sulfimide moiety, or an amineimine moiety have a high biocidal activity even under conditions not favorable to oxidizing biocides. The efficacy of these biocides is higher than the efficacy exhibited by chloramines derived from inorganic salts.

Series 9

Procedure:

Diluted procedure: Biocides were prepared from a solution of sodium hypochlorite (24,000 ppm as total chlorine) and an equal volume of a solution containing an equimolar amount of a nitrogen-containing compound or salt thereof. Final concentration of hypochlorite immediately prior to mixing was therefore expected to be 12,000 ppm.

Concentrated procedure: Biocides were prepared from a solution of sodium hypochlorite (12,000 ppm as total chlorine) and a negligible volume of a concentrated solution (ammonium/DMH: 18% w/v; guanidium sulfate, 30% w/v; ammonium carbamate, 35.3% w/v; ammonium sulfamate, 26.1% w/v) containing an equimolar amount of a nitrogen-containing compound or salt thereof. Final concentration of hypochlorite immediately prior to mixing was therefore expected to be 12,000 ppm.

Biocide pH, concentration and % were measured 20 minutes after mixing of the components. The results are shown in Table 16.

TABLE 16

| Compound/salt | mode of addition | biocide pH | biocide concentration ppm as Cl$_2$ | biocide % yield (relative to Cl alone) |
|---|---|---|---|---|
| DMH | dil. | 12.63 | 7500 | 61.5 |
| DMH | conc. | 12.65 | 6000 | 49.2 |
| Guanidine | dil. | 12.1 | 12200 | 100 |
| Guanidine | conc. | 12.11 | 11200 | 91.8 |
| Carbamate | dil. | 10.57 | 11300 | 92.6 |
| Carbamate | conc. | 10.55 | 9990 | 81.9 |
| Sulfamic | dil. | 10.5 | 3600 | 29.5 |
| Sulfamic | conc. | 11.19 | 3900 | 32 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A biocide comprising

[NH$_3$Cl$^+$][NH$_3$COO$^-$]

formed by mixing at least one salt which is ammonium carbamate with an aqueous solution of a hypochlorite oxidant at a molar ratio of ammonium to hypochlorite of at least 1:1, wherein said biocide is formed at a pH of at least 9.0 and wherein said biocide has a pH of at least 9.0.

2. A biocide according to claim 1, wherein the concentration of said hypochlorite oxidant in said aqueous hypochlorite oxidant solution immediately prior to mixing with said at least one salt is not more than 24,000 ppm as total chlorine.

3. A biocide according to claim 1, wherein said at least one salt is in an aqueous solution at a concentration of 0.5-40% w/v immediately prior to mixing with said hypochlorite oxidant solution.

4. A biocide according to claim 1 wherein said hypochlorite oxidant is selected from the group consisting of alkaline and alkali earth metal hypochlorites, hypochlorite released to water from a stable chlorine carrier and hypochlorite formed in situ from chlorine gas, and mixtures thereof.

5. A biocide according to claim 1, wherein said hypochlorite oxidant is selected from the group consisting of lithium hypochlorite, sodium hypochlorite, calcium hypochlorite, magnesium hypochlorite and potassium hypochlorite.

6. A biocide according to claim 1, wherein said at least one salt is diluted prior to mixing with said hypochlorite oxidant.

7. A biocide according to claim 1, wherein said biocide is formed at a pH of at least 9.5.

8. A biocide according to claim 1, wherein said biocide is formed at a pH of at least 10.0.

9. A biocide according to claim 1, wherein said biocide is formed at a pH of at least 10.5.

10. A biocide according to claim 1, wherein said biocide is formed at a pH of at least 11.0.

11. A biocide comprising

[NH$_3$Cl$^+$][NH$_2$SO$_3^-$]

formed by mixing ammonium sulfamate with an aqueous solution of a hypochlorite oxidant at a molar ratio of ammonium to hypochlorite of at least 1:1, wherein said biocide is formed at a pH of at least 10.5 and wherein said biocide has a pH of at least 10.5.

12. A biocide according to claim 11, wherein the concentration of said hypochlorite oxidant in said aqueous hypochlorite oxidant solution immediately prior to mixing with said ammonium sulfamate is not more than 24,000 as total chlorine.

13. A biocide according to claim 11, wherein said ammonium sulfamate is in an aqueous solution at a concentration of 0.5-40% w/v immediately prior to mixing with said hypochlorite oxidant solution.

14. A biocide according to claim 11, wherein said hypochlorite oxidant is selected from the group consisting of alkaline and alkali earth metal hypochlorites, hypochlorite released to water from a stable chlorine carrier and hypochlorite formed in situ from chlorine gas, and mixtures thereof.

15. A biocide according to claim 11, wherein said hypochlorite oxidant is selected from the group consisting of lithium hypochlorite, sodium hypochlorite, calcium hypochlorite, magnesium hypochlorite and potassium hypochlorite.

16. A biocide according to claim 11, wherein said ammonium sulfamate is diluted prior to mixing with said hypochlorite oxidant.

17. A biocide according claim 11, wherein said biocide is formed at a pH of at least 11.0.

* * * * *

UNITED STATES PATENT AND TRADEMARK OFFICE
CERTIFICATE OF CORRECTION

PATENT NO. : 8,652,496 B2  
APPLICATION NO. : 12/731917  
DATED : February 18, 2014  
INVENTOR(S) : Ayala Barak Page 1 of 1

It is certified that error appears in the above-identified patent and that said Letters Patent is hereby corrected as shown below:

On the Title page, delete the entirety of item (63), Related U.S. Application Data, and insert --Continuation of application No. 11/056,405, filed on Feb. 14, 2005, now Pat. No. 7,837,883, which is a continuation-in-part of application No. PCT/IL2005/000039, filed on Jan. 12, 2005.--.

In the Specification

Delete the first paragraph at column 1, beginning at line 6, and insert

--This application is a continuation of U.S. patent application Ser. No. 11/056,405, filed Feb. 14, 2005, which is a continuation-in-part of PCT/IL2005/000039, filed Jan. 12, 2005, and claims the benefit of priority from U.S. Provisional Patent Application Ser. Nos. 60/536,851, 60/536,811, 60/536,853 and 60/536,852, all of which were filed on Jan. 14, 2004. The contents of all of these applications are incorporated herein by reference.--.

Signed and Sealed this  
Twenty-third Day of February, 2016

Michelle K. Lee  
*Director of the United States Patent and Trademark Office*